United States Patent [19]

Hasegawa et al.

[11] Patent Number: 5,319,076

[45] Date of Patent: Jun. 7, 1994

[54] OLIGOSACCHARIDE DERIVATIVES SUITABLE FOR ALPHA-AMYLASE DETERMINATION

[75] Inventors: Akira Hasegawa; Makoto Kiso, both of Gifu; Shinji Satomura, Osaka, all of Japan

[73] Assignee: Wako Pure Chemical Industries, Inc., Osaka, Japan

[21] Appl. No.: 15,851

[22] Filed: Feb. 10, 1993

[30] Foreign Application Priority Data

Feb. 14, 1992 [JP] Japan .................. 4-059759

[51] Int. Cl.$^5$ .................. C07H 15/00; C07H 17/00; C07H 17/02; C07H 15/14
[52] U.S. Cl. .................. 536/4.1; 536/17.2; 536/17.3; 536/17.4; 536/17.5; 536/18.5
[58] Field of Search .................. 536/4.1, 17.2, 17.3, 536/17.4, 17.5

[56] References Cited

U.S. PATENT DOCUMENTS 4,762,917  8/1988  Ikenake et al.

FOREIGN PATENT DOCUMENTS 0171960  7/1985  European Pat. Off.
0252525  7/1987  European Pat. Off.

OTHER PUBLICATIONS

J. Biochem. 97(4), pp. 997–082, 1985.
CA. 119(7):73025x Tokutake et al. Abs. JP05009196 (1993).
CA 118(13):124905y Tokutake et al. Abs. "Chem Pharm Bull" 40(9) 2531–6 (1992).
CA 109(15):129518y Fujita et al. Abstract of "J. Org. Chem" 53(19) 4520–2 (1988).
CA 112(7):53634x Fujita et al. Abstract "Bull Chem Soc. Japan" 62(10) 31504 (1989).

*Primary Examiner*—Herbert J. Lilling
*Attorney, Agent, or Firm*—Armstrong, Westerman, Hattori, McLeland & Naughton

[57] ABSTRACT

An oligosaccharide derivative of the formula:

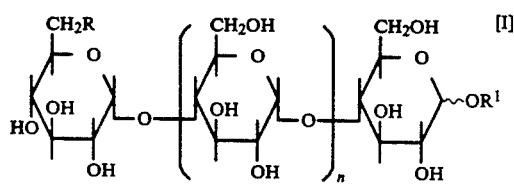

wherein R is $-SR^2$,

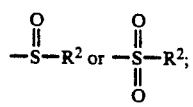

$R^1$ is an optically detectable group, etc.; $R^2$ is alkyl or substituted alkyl; and n is zero or 1–5, is effective as a substrate for measuring α-amylase activity and can be synthesized easily in high yield.

6 Claims, 2 Drawing Sheets

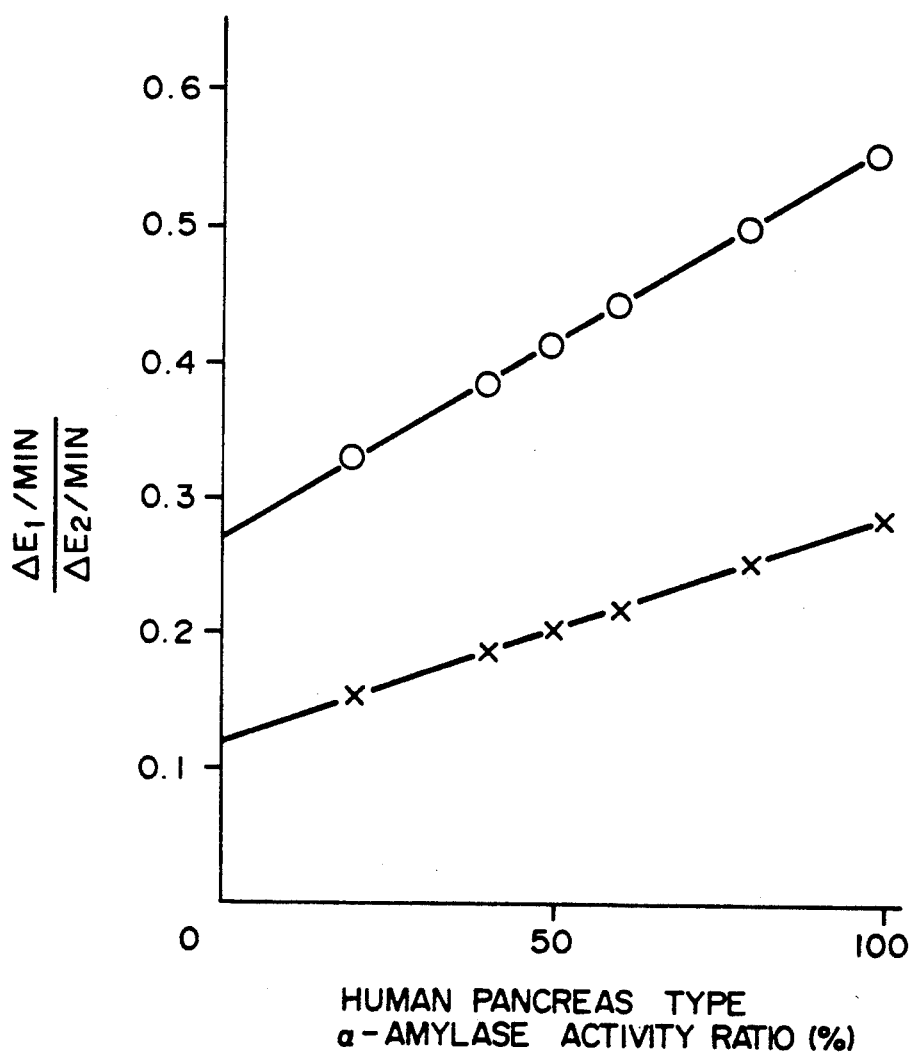
F I G. 2

OLIGOSACCHARIDE DERIVATIVES SUITABLE FOR ALPHA-AMYLASE DETERMINATION

BACKGROUND OF THE INVENTION

This invention relates to a non-reducing end modified oligosaccharide derivative useful as a substrate for measuring α-amylase activity, a process for producing the same, and α-amylase activity assay using said derivative as a substrate.

Measurement of α-amylase activity in samples, particularly in saliva, pancreatic juice, blood and urea in human living bodies is important in medical diagnosis. For example, α-amylase activity in blood and urea remarkably increases compared with a normal value when suffered from pancreatitis, cancer of the pancreas, and parotid gland. As to processes for measuring α-amylase activity, various processes have been reported. These processes can be divided into two groups, one of which uses long-chain natural products such as starch, amylose, amylopectin, etc. and modified materials thereof, and another of which uses oligosaccharides having 3 to 7 glucose residues.

Among these processes, there is widely used a coupling enzyme process using as a substrate maltooligosaccharide derivatives having a uniform structure and a clear substrate, that is, having a color forming group at the reducing end and having a modified group at the 6-position or 4- and 6-positions of the non-reducing end glucose unit. Since these substrates do not become a substrate for a coupling enzyme such as β-glucosidase, β-glucosidase, glucoamylase, etc. and the detection can be carried out by measuring the amount of colored substance released, they are particularly significant as substrates for measuring α-amylase activity. Particularly, maltooligosaccharide derivatives modified only at the 6-position of non-reducing end glucose and disclosed in Japanese Patent Unexamined Publication Nos. 63-170393 (EP 0252525) and 61-83196 (U.S. Pat. No. 4,762,917) are highly reactive as a substrate for α-amylase and excellent in storage stability, so that they are substrates for measuring α-amylase activity with almost high completeness. But they have a problem in that the conversion at the synthesis of these maltooligosaccharide derivatives is so low that they are not suitable for practical production.

Therefore, novel non-reducing end modified oligosaccharide derivatives capable of becoming excellent substrates for measuring o-amylase and able to be synthesized in a high yield are now desired.

SUMMARY OF THE INVENTION

It is an object of the present invention to provide a non-reducing and modified oligosaccharide derivative capable of becoming an excellent substrate for measuring α-amylase activity and being able to be synthesized in a high yield. It is another objects of the present invention to provide a process for producing such as oligosaccharide derivative and a process for using such an oligosaccharide derivative as a substrate for measuring α-amylase activity.

The present invention provides as oligosaccharide derivative of the formula:

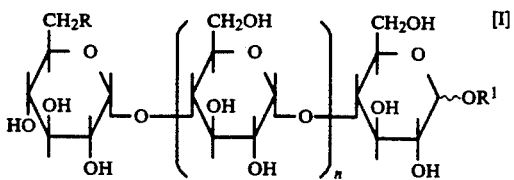

wherein R is $-SR^2$,

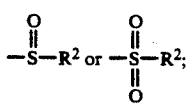

$R^2$ is an alkyl group or a substituted alkyl group; $R^1$ is an optically detectable group or a hydrogen atom; and n is zero or an integer of 1 to 5.

The present invention also provide a process for producing an oligosaccharide derivative of the formula:

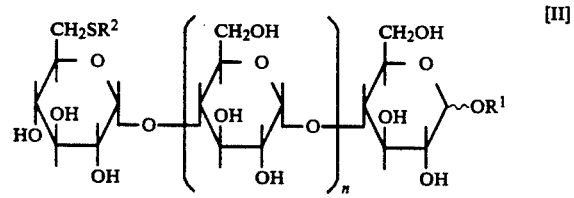

wherein $R^1$ is an optically detectable group or a hydrogen atom; $R^2$ is an alkyl group or a substituted alkyl group; and n is zero or an integer of 1 to 5, which comprises reacting an oligosaccharide derivative of the formula:

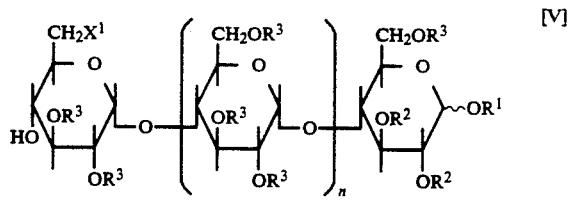

wherein $X^1$ is a halogen atom; $R^3$ is a hydrogen atom or an acyl group; and $R^1$, $R^2$ and n are as defined above, with thiocarboxylic acid or a salt thereof represented by the formula:

$R^4COSH$     [VI]

wherein $R^4$ is an alkyl group or a phenyl group, to introduce an acylthio group ($-SCOR^4$) into the 6-position of the non-reducing end glucose, conducting deacylation, and reacting with an alkyl halide or substituted alkyl halide of the formula:

$R^2X^2$     [VII]

wherein $X^2$ is a halogen atom; and $R^2$ is as defined above, or reacting with a compound of the formula:

$R^2OR_S$     [VIII]

wherein $R_S$ is a tosyl group (i.e. a p-toluenesulfonyl group), a brosyl group (i.e. a p-bromobenzenesulfonyl group), a trifluoromethanesulfonyl group or a mesyl group (i.e. methanesulfonyl group); and $R^2$ is as defined above.

The present invention further provides a process for producing an oligosaccharide derivative of the formula:

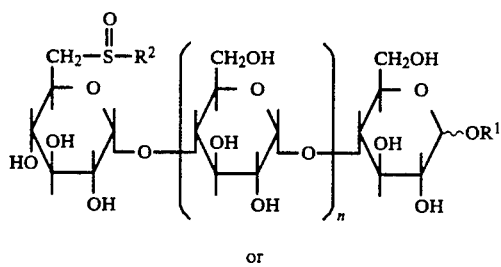 [III]

or

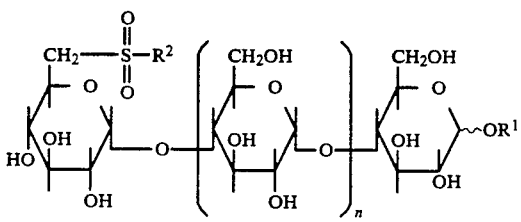 [II]

wherein $R^1$, $R^2$ and n are as defined above, which comprises oxidizing an oligosaccharide derivative of the formula:

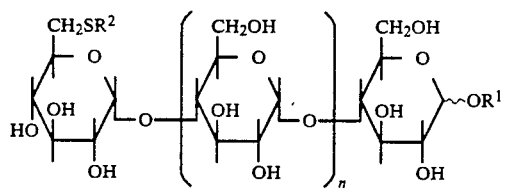 [II]

wherein $R^1$, $R^2$ and n are as defined above.

The present invention still further provides a process for measuring α-amylase activity using as a substrate an oligosaccharide derivative of the formula:

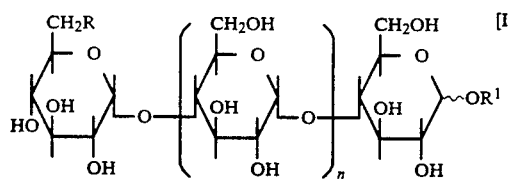 [I]

wherein R, $R^1$ and n are as defined above.

The present invention also provides a process for measuring α-amylase isozyme activities using as a substrate an oligosaccharide derivative of the formula:

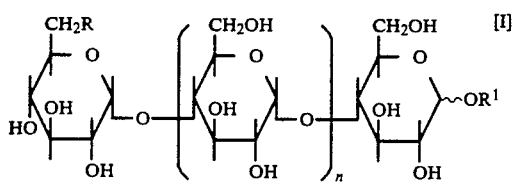 [I]

wherein R, $R^1$ and n are as defined above.

The present invention further provides a process for specifically measuring activity of α-amylase isozyme derived from human pancreas, which comprises measuring α-amylase activity using as a substrate an oligosaccharide derivative of the formula:

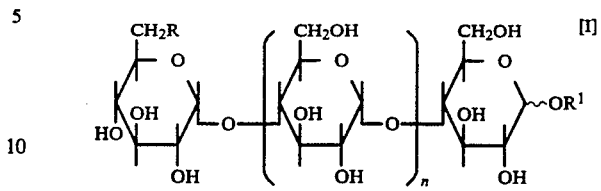 [I]

wherein R, $R^1$ and n are as defined above, in the presence of a substance which inhibits activity of α-amylase isozyme derived from human salivary gland.

BRIEF DESCRIPTION OF THE DRAWINGS

FIG. 2 is a graph showing a relationship between a ratio of changing rate of absorbance in a first reagent to that in a second reagent, and percentage of α-amylase activity of human pancreas in a sample solution obtained in Example 49.

DESCRIPTION OF THE PREFERRED EMBODIMENTS

Figure 1:
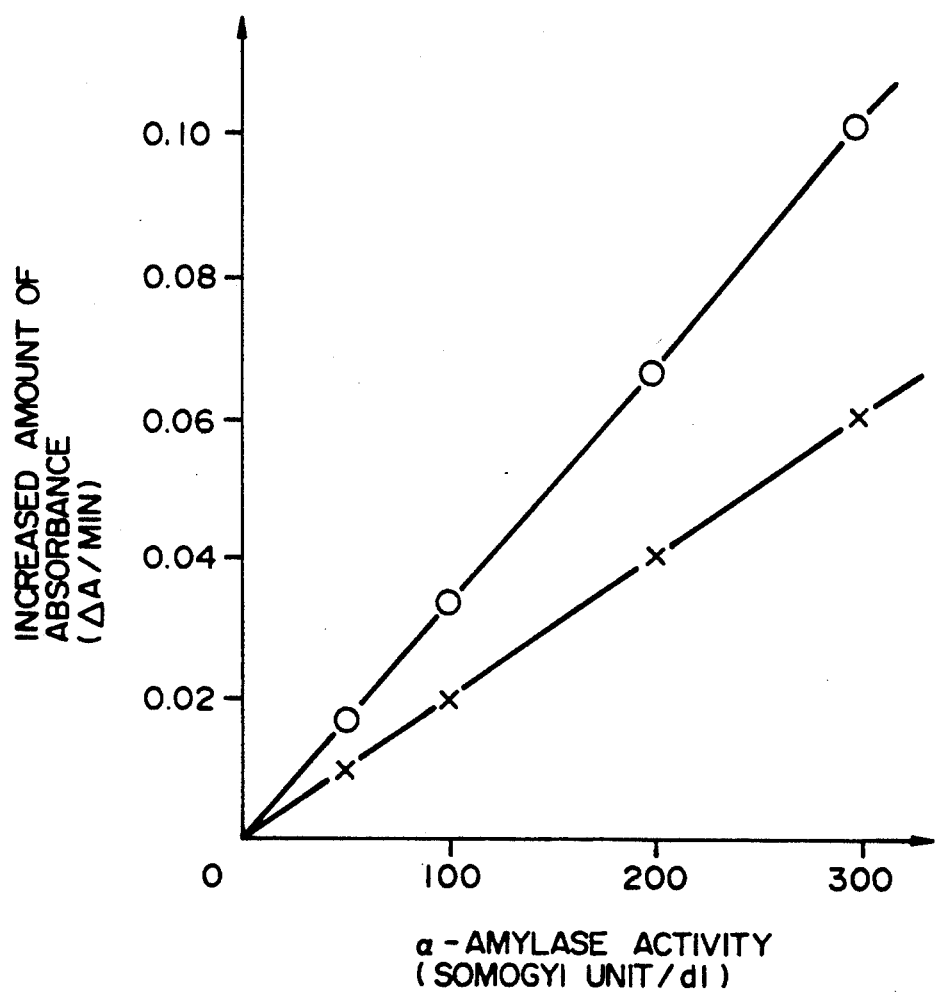
FIG. 1 is a graph showing a relationship between α-amylase activity and an increased amount of absorbance per minute at a wavelength of 405 nm obtained in Example 48.

The oligosaccharide derivative of the present invention can be used as a substrate for measuring α-amylase activity and can be synthesized in good yield compared with known ones. Such an oligosaccharide derivative is characterized by introducing an alkyl group or a substituted alkyl group into the 6-position of non-reducing end glucose via an S atom and represented by the formula:

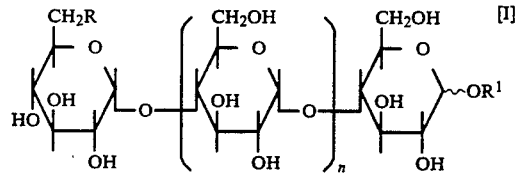 [I]

In the known oligosaccharide derivatives, various substituents are introduced into the 6-position of non-reducing end glucose only via an oxygen atom, not a sulfur atom as in the present invention. Thus, the oligosaccharide derivative of the formula [I] of the present invention is novel.

In the formula [I], R is —$SR^2$,

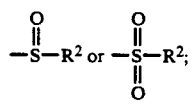

and $R^2$ is an alkyl group or a substituted alkyl group.

The alkyl group in the definition of $R^2$ is preferably a straight-chain or branched alkyl having 1 to 20 carbon atoms such as methyl, ethyl, propyl, butyl, amyl, hexyl, heptyl, octyl, nonyl, decyl, undecyl, dodecyl, pentadecyl, heptadecyl, octadenyl, icocyl, etc. Examples of the substituted alkyl group are straight-chain or branched alkyl preferably having 1 to 5 carbon atoms such as methyl, ethyl, propyl, butyl, amyl, etc. substituted with a non-substituted phenyl group, a substituted phenyl group (substituent being $C_{1-5}$ alkyl, $C_{1-5}$ alkoxy, etc.), an amino group, a substituted amino group (substituent being $C_{1-5}$ alkyl, $C_{2-5}$ hydroxyalkyl, $C_{2-5}$ sulfoalkyl, $C_{3-5}$ hydroxysulfoalkyl, etc.), heterocyclic groups such as a pyridyl group, a substituted pyridyl group (substituent being $C_{1-5}$ alkyl, $C_{1-5}$ alkoxy, amino, etc.), a piperidyl group, a piperadyl group, a morpholino group, etc.

$R^1$ in the formula [I] is an optically detectable group or a hydrogen atom. As the optically detectable group, there can be used groups which can be hydrolyzed by the action of coupling enzyme such as glucoamylase [E.C.3.2.1.3], α-glucosidase [E.C.3.2.1.20.], β-glucosidase [E.C.3.2.1.21.], isomaltose [E.C.3.2.1.10], β-amylase [E.C.3.2.1.2.], etc.; groups having absorption in the visible wavelength or ultraviolet wavelength by themselves after hydrolysis such as 4-nitrophenol, 2-chloro-4-nitrophenol, p-hydroxyacetophenone, 2-chloro-4-hydroxyacetophenone, etc.; groups emitting fluorescence by themselves such as umbelliferones; groups which produce colors by coupling with couplers by the action of oxidases such as catechol oxidase, laccase, tyrosinase, monophenol oxidase, etc.; groups which produce colors by coupling with couplers by the action of oxidizing agents; and the like. Examples of such optically detectable groups are conventionally used ones, e.g. aryl groups such as a phenyl group, 1-naphthyl group, 2-methylphenyl group, a 2-methyl-1-naphthyl group, etc.; substituted aryl groups, e.g. a 4-nitrophenyl group, a 3-nitrophenyl group, a 2-chlorophenyl group, a 4-chlorophenyl group, a 2,6-dichlorophenyl group, a 2-chloro-4-nitrophenyl group, a 4-acetylphenyl group, a 2-chloro-4-acetylphenyl group, a 2-methoxyphenyl group, a 4-methoxyphenyl group, a 2-carboxyphenyl group, a 2-sulfophenyl group, a 2-sulfo-1-naphthyl group, a 2-carboxy-1-naphthyl group, etc.; a umbelliferyl group; substituted umbelliferyl groups, e.g. a 4-methylumbelliferyl group, a 4-trifluoromethylumbelliferyl group, etc.; an indoxyl group; substituted indoxyl groups, e.g. a 5-bromoindoxyl group, a 4-chloro-3-bromoindoxyl group, etc. It is also possible to use a fructose residue of the formula:

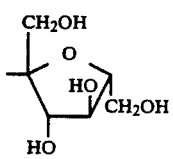

In this case, it is possible to measure α-amylase activity by optically measuring the degree of decrease of NADH produced by the reaction of mannitol dehydrogenase and NADH after hydrolysis by a coupling enzyme.

The oligosaccharide derivatives of the formula [I] include concretely the following three kinds of novel oligosaccharide derivatives of the formulae:

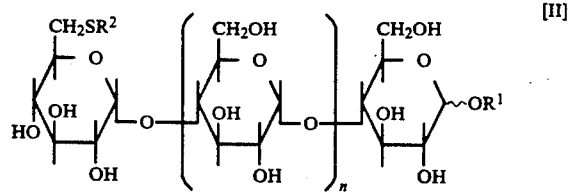

wherein $R^1$, $R^2$ and n are as defined above,

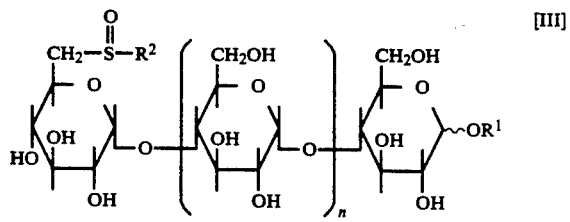

wherein $R^1$, $R^2$ and n are as defined above,

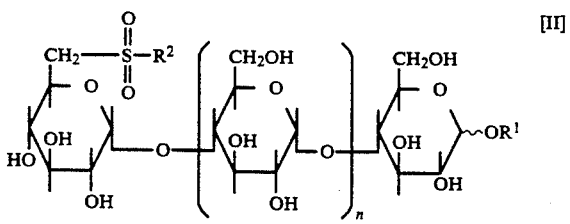

wherein $R^1$, $R^2$ and n are as defined above.

The oligosaccharide derivative of the formula [II] can be synthesized easily and in a high yield by using as a starting material an oligosaccharide of the formula:

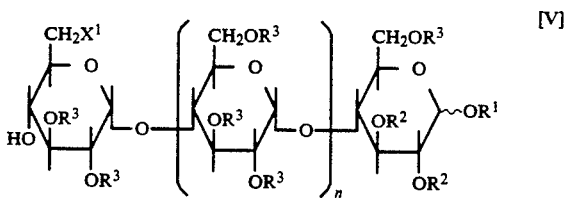

wherein $X^1$ is a halogen atom; $R^3$ is a hydrogen atom or an acyl group, e.g. acetyl, propionyl, benzoyl; and $R^1$, $R^2$ and n are as defined above. Particularly, the use of an acyl group as $R^3$ is preferable in order to enhance the solubility in a reaction solvent in the synthesis procedure.

More in detail, the oligosaccharide derivative of the formula [II] can be produced by reacting an oligosaccharide derivative of the formula [V] with thiocarboxylic acid or a salt thereof represented by the formula:

wherein $R^4$ is an alkyl group or a phenyl group, to introduce an acylthio group ($-SCOR^4$) into the 6-position of the non-reducing end glucose unit of the formula [V], conducting de-acylation reaction, followed by reaction with an alkyl halide or substituted alkyl halide of the formula:

wherein $X^2$ is a halogen atom; and $R^2$ is as defined above, or reaction with a compound of the formula:

$$R^2OR_S \qquad [VIII]$$

wherein $R_S$ is a tosyl group, a brosyl group, a trifluoromethanesulfonyl group or a mesyl group; and $R^2$ is as defined above.

In the above-mentioned synthesis, examples of the formula [VI] are thioacetic acid, potassium thioacetate, thiobenzoic acid, sodium thiobenzoate, etc. The compound of the formula [VI] is used in an amount of usually 1 to 10 moles, preferably 4 to 6 moles per mole of the compound of the formula [V].

The reaction of the compound of the formula [V] with the compound of the formula [VI] is carried out in an organic solvent, and in the case of using the compound of the formula [VI] in the form of acid, in the presence of 1 to 2 equivalent weight of a base such as NaOH, KOH, $Na_2CO_3$, $K_2CO_3$, sodium methoxide, sodium ethoxide, etc. per equivalent weight of the compound of the formula [VI]. Examples of the organic solvent are acetone, dioxane, N,N-dimethylformamide (DMF), dimethylacetamide, dimethylsulfoxide, dichloromethane, dichloroethane, etc. The reaction can be carried out with ice cooling, or upto 50° C. with slight heating, or at room temperature. The reaction time depends on the reaction temperature, the kind of solvent, and other reaction conditions, and is usually 3 or 4 hours to 50 or 60 hours. The progress of the reaction can be traced by TLC (thin-layer chromatography), etc. It is effective to co-use a dehydrating agent such as molecular sieves, drierite ($CaSO_4$), etc. As a result, the yield of 90% or more is usually obtained.

The resulting product having the acylthio group at the 6-position can be de-acylated when other hydroxyl groups are acyl protected (in the case of using a compound of the formula [V] wherein $R^3$ is an acyl group as a starting material).

The de-acylation reaction can be carried out by a conventional method, e.g. treatment with an alkali solution such as a 0.01-1.0N sodium methoxide.methanol solution, etc. for 3 to 60 hours at room temperature or slightly higher with heating (40° C.) or to a temperature with ice cooling.

The thus treated 6-position acylated form (acyl protected form or de-acyl protected form) is subjected to the reaction with the compound of the formula [VII] or the formula [VIII].

The reaction with the compound of the formula [VII] can be carried out by using the compound of the formula [VII] in an amount of usually 1 to 10 moles, preferably 1 to 2 moles per mole of the 6-position acylated form in a solvent such as methanol, dimethylsulfoxide (DMF), etc. under a nitrogen stream. The reaction temperature is usually −20° C. to +25° C., preferably −5° C. to 10° C. The reaction time changes depending on the reaction temperature, solvent and other conditions and are usually 3 to 60 hours. The reaction can be traced by TLC, etc.

Alternatively, the reaction with the compound of the formula [VIII] can be carried out by using the compound of the formula [VIII] in an amount of usually 1 to 10 moles, preferably 1 to 6 moles per mole of the 6-position acylated form in a solvent such as methanol, DMF, etc. under a nitrogen stream. The reaction temperature is usually −10° C. to 30° C., preferably 0° C. to 10° C. The reaction time changes depending on the reaction temperature, solvent and other conditions and are usually 3 to 60 hours. The reaction can be traced by TLC, etc.

When the reaction with the compound of the formula [VII] or formula [VIII] is carried out while retaining acyl protecting groups, it is necessary to conduct the de-acylation reaction after the reaction (the conditions and methods of the de-acylation reaction being as mentioned above).

Whether the de-acylation reaction or the reaction with the compound of the formula [VII] or the formula [VIII] is carried out first, it is possible to conduct the two reactions in one pot.

After-treatments after the reactions of individual steps can be carried out by conventional methods. The purification of the final product can be carried out by a conventional method such as column chromatography, etc.

The compound of the formula $R^2OR_S$ [VIII] can be produced easily by reacting an alcohol ($R^2OH$) with a halide ($R_SX^2$) in the presence of a base such as pyridine. Since many compounds of the formula $R^2OR_S$ are unstable, such compounds are usually used without isolation and purification, while removing only unreacted $R_SX^2$ by extraction, etc.

The compound of the formula [V] which is a starting material for the compound of the formula [II] can be produced by various methods. For example, Japanese Patent Unexamined Publication No. 63-170393 (EP 0252525) discloses the reaction of a halogen-modified cyclodextrin with cyclomaltodextrin glucanotransferase in the presence of an acceptor such as glucose, maltose, maltotriose, or a derivative thereof, followed by reaction with glucoamylase or α-glucosidase. Japanese Patent Unexamined Publication No. 4-154793 discloses the use of a polyacyloligosaccharide derivative retaining only a hydroxyl group at the 6-position of non-reducing end glucose unit as an intermediate. Japanese Patent Unexamined Publication No. 2-49796 (U.S. Pat. No. 5,011,923) and Japanese Patent Application No. 3-131880 disclose the use of polyacylmaltooligosaccharide derivatives retaining hydroxyl groups at the 4- and 6-positions of non-reducing end glucose unit as intermediates. Japanese Patent Examined Publication No. 62-51960 discloses a process via an oligosaccharide derivative wherein the 4- and 6-positions of non-reducing end glucose are subjected to benzylidene crosslinking.

The oligosaccharide derivatives of the formulae [III] and [IV] can easily be produced by oxidizing an oligosaccharide derivative of the formula [II].

The oxidization reaction can be carried out by using an oxidizing agent in an acidic solvent, an organic solvent or a mixed solvent of an acidic solvent and an organic solvent. As the oxidizing agent, there can be used any ones which can oxidize the sulfur atom to sulfoxide or sulfone, for example, m-chloroperbenzoic acid, hydrogen peroxide, peracetic acid, perbenzoic acid, etc. As the acidic solvent, there can be used acetic acid, formic acid, propionic acid, etc. As the organic solvent, there can be used dichloromethane, dichloroethane, chloroform, etc. A relatively low temperature, for example, about 10° to 25° C., is preferable for the reaction. The reaction time changes depending on the reaction temperature, solvent and other conditions, and is usually 4 or 5 minutes to 5 or 6 hours. The progress of the reaction can be traced by TLC, etc. The addition of the oxidizing agent is preferably carried out with cooling. Further, it is preferable to carry out the reaction in the dark. When the compound of the formula [II] is oxidized by using the above-mentioned oxidizing agents, the product is usually a mixture of a sulfoxide (the compound of the formula [III]) and a sulfone (the compound of the formula [IV]). By adjusting the amount of oxidizing agent to be added, the production ratio of the sulfoxide and the sulfone can be adjusted. That is, by addition of 1 equivalent weight or less of the oxidizing agent, the sulfoxide can predominantly be produced, and by addition of 2 equivalent weight or more of the oxidizing agent, the sulfone can predominantly be produced.

After the reaction, the reaction product is extracted with a polar solvent such as water, washed with an organic solvent such as dichloromethane, dichloroethane, chloroform, etc. under acidic conditions, and purified by a conventional method such as column chromatography, etc. In the case of sulfoxide, since there is usually obtained a mixture of isomers of S form and R form, the separation is effectively be carried out by high performance liquid chromatography (HPLC) using, for example, reverse phase column, etc.

Heretofore, a method of introducing an alkyl group into the 1-position of oligosaccharide via a sulfur atom is known, but the introduction of an alkyl group, etc. into the 6-position of non-reducing end glucose unit via a sulfur atom is novel and not disclosed in any prior art references.

As mentioned above, according to the present invention, the non-reducing end modified oligosaccharide derivatives useful as a substrate for measuring α-amylase activity, or as a substrate for measuring individual isozymes of human α-amylase.

One example of principles of measuring α-amylase activity using as a substrate the oligosaccharide derivative of the formula [I] is explained below.

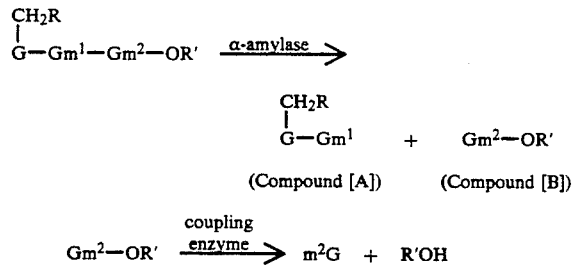

In the above equation, G is a glucose unit; R is a substituent at the 6-position of non-reducing end glucose unit; $m^1$ and $m^2$ are individually zero or an integer of 1 to 6 and the total of $m^1 + m^2$ is 1 to 6; and R' is an optically detectable group and substituted at the 1-position of reducing end glucose unit.

As shown in the above equation, α-amylase in a sample reacts with an oligosaccharide derivative of the formula [I] to produce the compound of the formula [A] wherein the 6-position of non-reducing end glucose has the substituent R and the compound of the formula [B] wherein the 1-position of reducing end glucose has an optically detectable group. Then, by the action of 1 to 3 kinds of coupling enzymes such as glucoamylase, α-glucosidase, β-glucosidase and isomaltose on the compound [B], $m^2G$ and R'—OH are produced. By measuring absorption spectra or fluorescence intensity derived from R'—OH, α-amylase activity in each sample can be obtained. For example, when R'—OH is a nitrophenol such as p-nitrophenol, absorption spectrum can directly be measured (e.g. absorbance at 405 nm). When R'—OH is a phenol or naphthol (either having a nitro group or not having a nitro group) such as phenol, o-chlorophenol, 2,6-dichlorophenol, p-methoxyphenol, etc., it is reacted with an oxidase such as catechol oxidase, laccase, tyrosinase, or monophenol oxidase, an oxidizing agent such as iodic acid or periodic acid, or peroxidase, and hydrogen peroxidase to conduct coupling (oxidative condensation) with a coupler such as 4-aminoantipyrine, 3-methyl-2-benzothiazolinonehydrazone (MBTH), etc. to produce a color, of which absorption spectrum is measured. When R'—OH is a compound emitting fluorescence such as umbelliferon, 4-methylumbelliferon, etc., its fluorescence is measured. When R'—OH is indoxyl, an absorption spectrum of indigo dye produced by oxidation is measured.

Another example of measuring α-amylase activity using the oligosaccharide derivative of the formula [I] as a substrate is to produce a dye directly without via a coupling enzyme in the presence of an activating agent such as hydrogen azide, an azide (e.g. alkali metal salts, alkaline earth metal salts of hydrogen azide) as disclosed in Japanese Patent Unexamined Publication No. 63-183595 (U.S. Pat. Nos. 4,963,479 and 5,158,872). As the activating agent, it is also possible to use thiocyanic acid salts (e.g. KSCN, NaSCN, etc.), cyanic acid salts (e.g. KCNO, etc.).

When an oligosaccharide derivative having no modifying group at the non-reducing end glucose unit as disclosed in U.S. Pat. Nos. 4,963,479 or 5,158,872 is used as a substrate, transglycosylation is brought about by α-amylase to produce various substrates having different numbers of glucose units. Thus, only a part of hydrolyzed products by α-amylase can be measured. Further, since various kinds of substrates are produced, there arises a problem of making the reaction complicated. In contrast, when the oligosaccharide derivative of the formula [I] is used as a substrate, the disadvantages mentioned above are not caused.

The concentration of the oligosaccharide derivative of the formula [I] used as a substrate in the measurement of α-amylase activity is not particularly limited, but preferably 0.1 to 30 mM.

As the samples to be subjected to measurement of α-amylase activity using the oligosaccharide derivative of the formula [I] as a substrate, any samples can be used so long as containing α-amylase, for example, living body components such as saliva, pancreatic juice, blood, serum, urine, etc.

Coupling enzymes such as glucoamylase, α-glucosidase, β-glucosidase and isomaltose are not particularly limited, and any ones derived from animals, plants and microorganisms can be used singly or in combination. The using amount of the coupling enzyme is usually 0.5 to 1000 U/ml, preferably 2 to 500 U/ml.

When a measuring process using no coupling enzyme is carried out, it is preferable to use the oligosaccharide derivative of the formula [I] wherein n is 0 or 1 or 2, more preferably n is 1 or 2. In this case, it is usual to add an azide, a thiocyanic acid salt, etc. known as an activating agent for α-amylase. According to the present invention, the same effect as mentioned above can also be obtained by adding an alkali metal salt such as sodium chloride, potassium chloride, etc. or cyanic acid salt such as KCNO. The concentration of the activating agent is usually about 50 mmol/l. to 10 mol/l.

The reaction temperature used in the measurement of α-amylase activity is preferably about 25° to 40° C. The reaction time can be selected properly depending on purposes.

A suitable pH for the measurement of α-amylase activity is preferably about 6 to 8. In order to maintain the preferable pH, it is possible to add a buffer such as a phosphate buffer, a Tris-hydroxymethyl aminomethane-HCl buffer, a Good's buffer, etc.

As the activating agent for α-amylase, there can be used various compounds. When the oligosaccharide derivative of the formula [I] wherein n is 3 or more is used as a substrate, there are used, for example, sodium chloride, calcium chloride, potassium chloride, etc. When the oligosaccharide derivative of the formula [I] wherein n is 2 or less is used as a substrate, there are used azides, thiocyanic acid salts, cyanic acid salts, alkali metal salts such as sodium chloride, potassium chloride, etc. singly or in combination.

As the coupler for coupling (oxidative condensation) with a free phenol or naphthol by the action of coupling enzyme, there can be used 4-aminoantipyrine, 3-methyl-2-benzothiazolinonehydrazone (MBTH), p-amino-N,N-diethylaniline, etc.

As the oxidase used for coupling a phenol or naphthol with a coupler, there can be used laccase, catecholoxidase, tyrosinase, monophenol oxidase, etc. derived from animals, plants, microorganisms. The concentration of the oxidase used is usually 0.2 to 10 U/ml, preferably 0.5 to 4 U/ml.

As the oxidizing agent used for the coupling (oxidative condensation), there can be used iodic acid, salts thereof, periodic acid, salts thereof, hydrogen peroxide, etc.

The oligosaccharide derivative of the formula [I] has the R group in place of a hydroxyl group at the 6-position of non-reducing end glucose unit, so that it cannot be used as it is as a substrate for glucoamylase, α-glucosidase, β-glucosidase, or isomaltase. Further, since many of the oligosaccharide derivatives of the formula [I] are easily soluble in water and excellent in affinity to α-amylase, they can become good specific substrates for α-amylase.

Therefore, in the measuring process for α-amylase activity using the oligosaccharide derivative of the formula [I] as a substrate, side reactions do not take place, a reagent blank value is extremely small and a reagent solution for the measurement is remarkably stable. Further, since a single compound is used as a substrate, stoichiometry of the reaction is established so as to make it possible to conduct kinetic detection.

Further, since coupling enzymes such as glucoamylase, α-glucosidase, β-glucosidase or isomaltase can sufficiently be used in the measurement of α-amylase activity using the oligosaccharide derivative of the formula [I], α-amylase activity can be measured accurately with high sensitivity due to fast reaction rate after the α-amylase reaction.

In addition, according to the α-amylase activity measuring process of the present invention, since the optical measurement is carried out by measuring absorption spectra of nitrophenols, p-hydroxyacetophenols or indigo dyes released, by measuring absorption spectra of dyes obtained by oxidative coupling of a phenol or a naphthol released with 4-aminoantipyrine, MBTH, etc., or by measuring fluorescence intensity of an umbelliferon released, influences of sugars such as glucose, maltose, etc. and reducing substances such as ascorbic acid, bilirubin, etc. present in samples hardly appear.

As the measuring process for α-amylase activity, there can be used either a rate assay wherein the reaction rate at predetermined conditions is measured, or an end-point assay wherein a reaction stopper is used.

Further, the α-amylase activity measuring process of the present invention can be conducted using an autoanalyzer, or if necessary by a manual method.

In addition, when the oligosaccharide derivative of the formula [I] is used as a substrate, it is possible to employ the measurement of coloring of dyes, that is, to conduct a calorimetric method. Thus, the measuring method for α-amylase activity can be applied to a simple test paper method, and a so-called dry quantitative method using a multi-layer analysis sheet containing reaction reagents (an integral multi-layered quantitative analysis film).

The oligosaccharide derivative of the formula [I] can also be used as an effective substrate in a measuring process of α-amylase isozymes derived from human salivary gland and α-amylase derived from human pancreas as disclosed in Japanese Patent Unexamined Publication No. 63-39600 (EP 0260414). In such a process, a decomposed product produced by hydrolyzing action of α-amylase is reacted with two or more coupling enzymes having different specificity for the substrate, followed by measurement of the products so as to carry out differentiation measurement of α-amylase derived from human pancrease and α-amylase derived from human salivary gland.

When the oligosaccharide derivative of the formula [I] wherein n is 1 or 2 is used as a substrate, a discrimination or differentiation measurement of α-amylase isozymes can be carried out by using only one kind of coupling enzyme. The measuring principle is explained below referring to the case wherein n is zero.

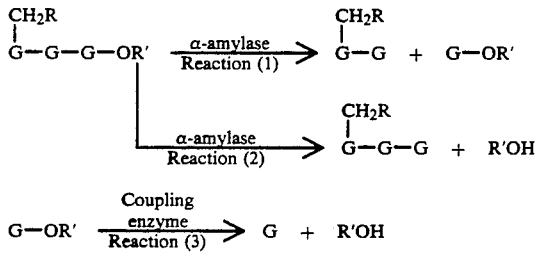

In the above equation, G, R and R' are as defined above. When α-amylase in a sample acts on the oligosaccharide derivative of the formula [I] wherein n is 1, the Reaction (1) and Reaction (2) take place depending on the kind of R group in a certain proportion. R'—OH is produced by the Reaction (2). Then, when one or more coupling enzymes such as α-glucosidase, β-glucosidase, isomaltase, etc. act on a reaction product of the Reaction (1), R'—OH is produced from G—OR' by the Reaction (3).

After obtaining a ratio of the amount of R'—OH (per unit time) produced by the Reaction (2) to the total amount of R'—OH (per unit time) produced by the Reaction (3), the differentiation measurement of α-amylase isozymes can be carried out according to the method disclosed in Japanese Patent Unexamined Publication No. 61-181564 based on the obtained ratio. In such a case, it is desirable to add an α-amylase activating agent such as an azide, a thiocyanic acid salt, a cyanic acid salt, sodium chloride, potassium chloride, etc.

The oligosaccharide derivative of the formula [I] can also be used as a substrate for measuring pancreas type α-amylase activity wherein the activity of α-amylase derived from human pancreas (pancreas type α-amylase) is specifically measured in the presence of an inhibiting substance for α-amylase derived from human salivary gland (saliva type α-amylase). In such a case, it is possible to add an α-amylase activating agent such as an azide, a thiocyanic acid salt, a cyanic acid salt, sodium chloride, potassium chloride, etc., according to a conventional method, if necessary.

As the inhibiting substance for saliva type α-amylase, there can be used, for example, an inhibitor derived from wheat germ, monoclonal antibody which specifically inhibits the saliva type α-amylase described in Clin. Chem. 28/7, pp. 1525-1527 (1982). The monoclonal antibody mentioned above is described in, for example, Japanese Patent Unexamined Publication Nos. 58-183098, 60-155134 (U.S. Pat. No. 4,939,082), 61-164161 (U.S. Pat. No. 5,071,744) and 61-194365 and Japanese Patent Examined Publication No. 63-2600 (EP 209154). When monoclonal antibody is used, it is possible to use two or more monoclonal antibodies having different activities, if necessary.

The present invention is illustrated by way of the following Examples.

EXAMPLE 1

Synthesis of p-nitrophenyl o-(6-S-benzyl-6-thio-α-D-glucopyranosyl)-(1→4)-tris{o-α-D-glucopyranosyl-(1→4)}-α-D-glucopyranoside (Compound No. 1) of the formula:

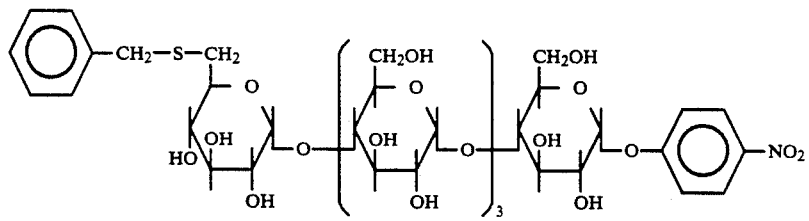

(1) Synthesis of p-nitrophenyl O-(2,3,4-tri-O-acetyl-6-S-acetyl-6-trio-α-D-glucopyranosyl)-(1-4)-tris{O-(2,3,6-tri-O-acetyl-α-D-glucopyranosyl)-(1→4)}-2,3,6-tri-O-acetyl-α-D-glucopyranoside (Fullacetyl-AsSG5P) of the formula:

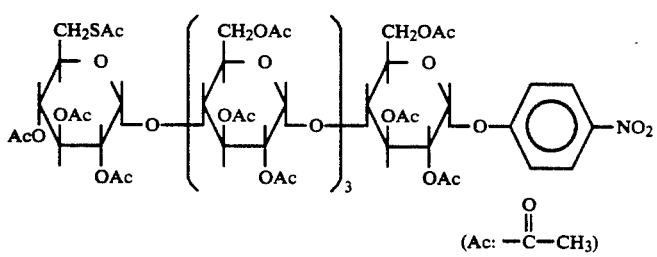

According to the method described in Japanese Patent Unexamined Publication No. 63-170393, p-nitrophenyl O-(6-bromo-6-deoxy)-α-D-glucopyranosyl-(1→4)-O-α-D-glucopyranosyl-(1→4)-O-α-D-glucopyranosyl-(1→4)-O-α-D-glucopyranosyl-(1→4)-α-D-glucopyranoside (BrG5P) was synthesized. Then, 5.97 g of p-nitrophenyl O-(2,3,4-tri-O-acetyl-6-bromo-6-deoxy)-α-D-glucopyranosyl-(1-4)-tris{O-(2,3,6-tri-O-acetyl-α-D-glucopyranosyl)-(1→4)}-3,4,6-tri-O-acetyl-α-D-glucopyranoside (Fullacetyl-BrG5P) obtained by acetylating BrG5P by a conventional method was dissolved in 180 ml of dry acetone, and added with 6 g of drierite and 40 g of potassium thioacetate, followed by stirring at 25° C. overnight. The end of the reaction was confirmed by TLC (double development solvent used: dichloromethane:methanol=60:1 v/v). Then, the drierite was removed by filtration, and washed with dichloromethane. The filtrate and the washed solution were combined and concentrated under reduced pressure. The resulting sirup was subjected to column chromatography [Wakogel C-200 (a trade name, mfd. by Wako Pure Chemical Industries, Ltd.); eluents: (a) dichloromethane, (b) dichloromethane/methanol=300/1, (c) dichloromethane/methanol=100/1] to give 5.54 g (yield 93%) of Fullacetyl-AcSG5P from the eluent (c).

(2) Synthesis of Compound No. 1

To a solution obtained by dissolving Fullacetyl-AsSG5P in an amount of 0.294 mmol in methanol, a methanol solution containing 0.294 mmol of sodium methoxide was added and allowed to stand at 25° C. After confirming the production of de-acetylated form by TLC (butanol:ethanol:water=4:2:1 v/v/v), 0.294 mmol of benzyl bromide was added thereto, followed by stirring at 40° C. under a nitrogen stream. After confirming the end of reaction by TLC (butanol:ethanol:water=4:2:1 v/v/v), the reaction solution was concentrated at 30° C. under reduced pressure. The resulting sirup was subjected to column chromatography [Sephadex LH-20 (a trade name mfd. by Parmacia LKB Biotechnology); eluent:methanol] to give 145 mg of Compound No. 1. The reaction yield and the angle of rotation are shown in Table 1. Further, the results of IR and $^1$H-NMR are shown in Table 2.

EXAMPLES 2 TO 34

Various oligosaccharide derivatives of the formula [II] (Compound Nos. 2-34) were synthesized in the same manner as described in Example 1 except for using as a stanting material those as shown in Table 1 in place of benzyl bromide used in Example 1.

The yields and angles of rotation of the resulting compounds are shown in Table 1. Further, the results of IR and $^1$H-NMR are also shown in Table 2.

TABLE 1

| Compound No. | Starting material | Compound of Formula [II] R² | R¹ | n | Yield % | Angle of rotation $[\alpha]_D$ (MeOH) |
|---|---|---|---|---|---|---|
| 1 | Br—CH₂—C₆H₅ | —CH₂—C₆H₅ | —C₆H₄—NO₂ | 3 | 47 | +182° |
| 2 | Cl—CH₂—C₆H₄—CH₃ | —CH₂—C₆H₄—CH₃ | " | 3 | 68 | +198° |
| 3 | Cl—CH₂—C₆H₄—C(CH₃)₃ | —CH₂—C₆H₄—C(CH₃)₃ | " | 3 | 79 | +182° |
| 4 | Br—CH₂—CH₂—C₆H₅ | —CH₂—CH₂—C₆H₅ | " | 3 | 65 | +168° |
| 5 | Br—*CH(CH₃)—C₆H₅ (racemic modification) | —C(CH₃)(H)—C₆H₅  I (S) | " | 3 | I + II 60 | +116° |
|   |   | —C(CH₃)(H)—C₆H₅  II (R) | " | 3 |   | +221° |
| 6 | Br—CH₂—CH₃ | —(CH₂)ₙ—CH₃ n = 1 | " | 3 | 56 | +166° |
| 7 | Br—(CH₂)₂—CH₃ | —(CH₂)ₙ—CH₃ n = 2 | " | 3 | 65 | +183° |
| 8 | Br—(CH₂)₃—CH₃ | —(CH₂)ₙ—CH₃ n = 3 | " | 3 | 46 | +176° |
| 9 | Br—(CH₂)₄—CH₃ | —(CH₂)ₙ—CH₃ n = 4 | " | 3 | 62 | +172° |
| 10 | Br—(CH₂)₅—CH₃ | —(CH₂)ₙ—CH₃ n = 5 | " | 3 | 74 | +174° |
| 11 | Br—(CH₂)₆—CH₃ | —(CH₂)ₙ—CH₃ n = 6 | " | 3 | 67 | +183° |
| 12 | Br—(CH₂)₁₁—CH₃ | —(CH₂)ₙ—CH₃ n = 11 | " | 3 | 50 | +163° |
| 13 | Br—(CH₂)₁₇—CH₃ | —(CH₂)ₙ—CH₃ n = 17 | " | 3 | 35 | +139° |
| 14 | Br—CH(CH₃)—CH₃ | —CH(CH₃)—CH₃ | —C₆H₄—NO₂ | 3 | 32 | +179° |
| 15 | Br—CH₂—CH(CH₃)—CH₃ | —CH₂—CH(CH₃)—CH₃ | " | 3 | 31 | +179° |
| 16 | Br—*CH(CH₃)—CH₂—CH₃ (racemic modification) | —*CH(CH₃)—CH₂—CH₃ (racemic modification) | " | 3 | 13 | +179° |
| 17 | Br—CH₂—CH₂—CH(CH₃)—CH₃ | —CH₂—CH₂—CH(CH₃)—CH₃ | " | 3 | 45 | +179° |

TABLE 1-continued

| Compound No. | Starting material | Compound of Formula [II] R² | R¹ | n | Yield % | Angle of rotation [α]_D (MeOH) |
|---|---|---|---|---|---|---|
| 18 | Cl—CH₂—CH₂—N(CH₂—CH₃)₂ .HCl | —CH₂—CH₂—N(CH₂—CH₃)₂ | " | 3 | 71 | +127° |
| 19 | Cl—CH₂—CH₂—N(CH₃)₂ .HCl | —CH₂—CH₂—N(CH₃)₂ | " | 3 | 51 | +130° |
| 20 | Cl—CH₂—CH₂—CH₂—N(CH₃)₂ .HCl | —CH₂—CH₂—CH₂—N(CH₃)₂ | " | 3 | 22 | +121° |
| 21 | Cl—CH₂—CH₂—N(piperidine) .HCl | —CH₂—CH₂—N(piperidine) | " | 3 | 63 | +112° |
| 22 | Cl—CH₂—CH₂—CH₂—N(piperidine) .HCl | —CH₂—CH₂—CH₂—N(piperidine) | " | 3 | 31 | +126° |
| 23 | Cl—CH₂—CH₂—N(morpholine) .HCl | —CH₂—CH₂—N(morpholine) | " | 3 | 69 | +125° |
| 24 | Cl—CH₂—CH₂—CH₂—N(piperazine-NH) .2HCl | —CH₂—CH₂—CH₂—N(piperazine-NH) | " | 3 | 5 | +138° |
| 25 | Cl—CH₂-(2-pyridyl) .HCl | —CH₂-(2-pyridyl) | " | 3 | 69 | +111° |
| 26 | Cl—CH₂-(pyridyl) .HCl | —CH₂-(pyridyl) | p-NO₂-phenyl | 3 | 71 | +161° |
| 27 | Cl—CH₂-(4-pyridyl) .HCl | —CH₂-(4-pyridyl) | " | 3 | 87 | +167° |
| 28 | o-NO₂-benzyl-Br | o-NO₂-benzyl—CH₂— | " | 3 | 70 | +148° |
| 29 | Cl—CH₂—CH₂—N(piperidine) .HCl | —CH₂—CH₂—N(piperidine) | " | 3 | 81 | +130.6° |

Note
1) The mark "*" shows an asymmetric center.
2) (S) and (R) show steric configurations.

TABLE 1-continued

| Compound No. | Starting material | Compound of Formula [II] R² | R¹ | n | Yield % | Angle of rotation [α]_D (MeOH) |
|---|---|---|---|---|---|---|
| 30 | Br—CH₂—CH₂—CH₂—Ph | —CH₂—CH₂—CH₂—Ph | " | 3 | 81 | +164°* |
| 31 | I—CH₃ | —CH₃ | " | 3 | 85 | +164° |
| 32 | Br—CH₂—Ph | —CH₂—Ph | 3-Cl-4-NO₂-phenyl | 1 | 67 | +117° |
| 33 | " | " | " | 2 | 31 | +156° |
| 34 | " | " | " | 3 | 33 | |

Note
*measured in dioxane:H₂O = 5:1 v/v

TABLE 2

| Compound No. | IR (KBr) νcm⁻¹ | | ¹H-NMR (CD₃OD): δppm | |
|---|---|---|---|---|
| 1 | 3400, 1010<br>2900<br>1510, 1340, 850<br>700 | (OH)<br>(CH₃CH₂)<br>(p-nitrophenyl)<br>(phenyl) | 2.52<br>2.85<br>3.20<br>4.10<br>5.12<br>5.13, 5.15<br>5.21<br>5.66<br>7.18~7.34<br>7.31<br>8.22 | (dd, 1H, J=7.9 and 11.9Hz)<br>(dd, 1H, J=2.1 and 11.9Hz)<br>(t, 1H, J=9.3Hz)<br>(t, 1H, J=8.9Hz)<br>(d, 1H, J=4.0Hz)<br>(2d, 2H, J=4.3Hz)<br>(d, 1H, J=3.9Hz)<br>(d, 1H, J=3.5Hz)<br>(m, 5H)<br>(2d, 2H, J=9.2Hz)<br>(2d, 2H, J=9.3Hz) |
| 2 | 3400, 1010<br>2900<br>1510, 1340, 850<br>700 | (OH)<br>(CH₃CH₂)<br>(p-nitrophenyl)<br>(phenyl) | 2.28<br>2.51<br>2.83<br>3.19<br>4.10<br>5.11<br>5.13, 5.15<br>5.20<br>5.66<br>7.05~7.19<br>7.31<br>8.21 | (s, 3H)<br>(dd, 1H, J=7.9 and 11.7Hz)<br>(dd, 1H, J=3.9 and 12.0Hz)<br>(t, 1H, J=9.3Hz)<br>(t, 1H, J=9.0Hz)<br>(d, 1H, J=3.5Hz)<br>(2d, 2H, J=4.0Hz)<br>(d, 1H, J=3.8Hz)<br>(d, 1H, J=3.7Hz)<br>(m, 4H)<br>(2d, 2H, J=9.3Hz)<br>(2d, 2H, J=9.3Hz) |
| 3 | 3400, 1010<br>2900<br>1510, 1340, 850<br>700 | (OH)<br>(CH₃CH₂)<br>(p-nitrophenyl)<br>(phenyl) | 1.29<br>2.51<br>2.86<br>3.18<br>4.10<br>5.09<br>5.13, 5.14<br>5.19<br>5.65<br>7.20~7.39<br>7.31<br>8.22 | (s, 9H)<br>(dd, 1H, J=8.0 and 12.0Hz)<br>(dd, 1H, J=2.0 and 12.5Hz)<br>(t, 1H, J=9.3Hz)<br>(t, 1H, J=9.9Hz)<br>(d, 1H, J=3.7Hz)<br>(2d, 2H, J=3.7Hz)<br>(d, 1H, J=3.9Hz)<br>(d, 1H, J=3.7Hz)<br>(m, 4H)<br>(2d, 2H, J=9.3Hz)<br>(2d, 2H, J=9.4Hz) |
| 4 | 3350, 1020<br>2940<br>1520, 1350, 850<br>700 | (OH)<br>(CH₂)<br>(p-OPhNO₂)<br>(Ph) | 2.63<br>2.83<br>3.01<br>3.22<br>4.11<br>5.10<br>5.13, 5.14<br>5.21<br>5.66<br>7.12~7.28<br>7.30<br>8.21 | (dd, 1H, J=7.7 and 12.2Hz)<br>(broad s, 4H)<br>(dd, 1H, J=2.1 and 14.3Hz)<br>(t, 1H, J=9.2Hz)<br>(t, 1H, J=8.4Hz)<br>(d, 1H, J=3.8Hz)<br>(2d, 2H, J=4.3Hz)<br>(d, 1H, J=3.9Hz)<br>(d, 1H, J=3.7Hz)<br>(m, 5H)<br>(2d, 2H, J=9.3Hz)<br>(2d, 2H, J=9.3Hz) |
| 5<br>I<br>S | 3400, 1020<br>2940<br>1520, 1350, 850<br>700 | (OH)<br>(CH₃, CH₂, CH)<br>(p-OPhNO₂)<br>(Ph) | 1.50<br>2.38<br>2.78<br>3.09 | (d, 3H, 7=7.1Hz)<br>(dd, 1H, J=8.2 and 11.4Hz)<br>(dd, 1H, J=2.3 and 11.9Hz)<br>(t, 1H, J=9.4Hz) |

TABLE 2-continued

| Compound No. | IR (KBr) νcm$^{-1}$ | | $^1$H-NMR (CD$_3$OD): δppm | |
|---|---|---|---|---|
| | | | 4.097 | (q, 1H, J=7.1Hz) |
| | | | 4.104 | (t, 1H, J=8.8Hz) |
| | | | 5.09 | (d, 1H, J=3.5Hz) |
| | | | 5.12, 5.15 | (2d, 2H, J=3.7Hz) |
| | | | 5.20 | (d, 1H, J=3.5Hz) |
| | | | 5.66 | (d, 1H, J=3.3Hz) |
| | | | 7.17~7.30 | (m, 5H) |
| | | | 7.31 | (2d, 2H, J=9.2Hz) |
| | | | 8.21 | (2d, 2H, J=9.3Hz) |
| 5 | 3400, 1020 | (OH) | 1.50 | (d, 3H, J=7.0Hz) |
| II | 2940 | (CH$_3$, CH$_2$, CH) | 2.44 | (dd, 1H, J=7.0 and 12.3Hz) |
| | 1520, 1350, 860 | (p-OPhNO$_2$) | 2.68 | (dd, 1H, J=2.4 and 12.6Hz) |
| R form | 700 | (Ph) | 3.21 | (t, 1H, J=9.2Hz) |
| | | | 4.06 | (q, 1H, J=7.0Hz) |
| | | | 4.11 | (t, 1H, J=9.5Hz) |
| | | | 5.11 | (t, 1H, J=3.5Hz) |
| | | | 5.137, 5.144 | (2d, 2H, J=3.7Hz) |
| | | | 5.21 | (d, 1H, J=3.9Hz) |
| | | | 5.66 | (d, 1H, J=3.7Hz) |
| | | | 7.18~7.37 | (m, 5H) |
| | | | 7.32 | (2d, 2H, J=9.4Hz) |
| | | | 8.21 | (2d, 2H, J=9.2Hz) |
| 6 | 3400, 1020 | (OH) | 1.22 | (t, 3H, J=7.3Hz) |
| | 2940 | (Ethyl) | 2.60 | (2dd, 2H, J=7.3 and 13.1Hz) |
| | 1520, 1350, 880 | (p-nitrophenyl) | 2.62 | (dd, 1H, J=8.0 and 11.6Hz) |
| | | | 2.97 | (dd, 1H, J=2.6 and 14.0Hz) |
| | | | 3.20 | (t, 1H, J=9.3Hz) |
| | | | 4.11 | (t, 1H, J=8.4Hz) |
| | | | 5.09 | (d, 1H, J=3.7Hz) |
| | | | 5.13, 5.15 | (2d, 2H, J=4.4Hz) |
| | | | 5.21 | (d, 1H, J=3.7Hz) |
| | | | 5.66 | (d, 1H, J=3.7Hz) |
| | | | 7.33 | (2d, 2H, J=9.2Hz) |
| | | | 8.21 | (2d, 2H, J=9.2Hz) |
| 7 | 3400, 1020 | (OH) | 0.95 | (t, 3H, J=7.3Hz) |
| | 2940 | (Propyl) | 1.58 | (2dt, 2H, J=7.3 and 12.6Hz) |
| | 1520, 1340, 870 | (p-nitrophenyl) | 2.55 | (2t, 2H, J=7.3Hz) |
| | | | 2.59 | (dd, 1H, J=7.9 and 13.6Hz) |
| | | | 2.94 | (dd, 1H, J=~0 and 11.9Hz) |
| | | | 3.20 | (t, 1H, J=9.2Hz) |
| | | | 4.11 | (t, 1H, J=9.0Hz) |
| | | | 5.09 | (d, 1H, J=3.7Hz) |
| | | | 5.13, 5.15 | (2d, 2H, J=4.5Hz) |
| | | | 5.21 | (d, 1H, J=3.7Hz) |
| | | | 5.67 | (d, 1H, J=3.7Hz) |
| | | | 7.30 | (2d, 2H, J=9.4Hz) |
| | | | 8.21 | (2d, 2H, J=9.3Hz) |
| 8 | 3400, 1020 | (OH) | 0.90 | (t, 3H, J=7.2Hz) |
| | 2940 | (alkyl) | 1.35~1.49 | (m, 2H) |
| | 1520, 1340, 870 | (p-nitrophenyl) | 1.52~1.57 | (m, 2H) |
| | | | 2.57 | (2t, 2H, J=7.2Hz) |
| | | | 2.58 | (dd, 1H, J=8.0 and 11.7Hz) |
| | | | 2.94 | (dd, 1H, J=~0 and 11.7Hz) |
| | | | 3.20 | (t, 1H, J=9.3Hz) |
| | | | 4.11 | (t, 1H, J=9.2Hz) |
| | | | 5.09 | (d, 1H, J=3.8Hz) |
| | | | 5.13, 5.14 | (2d, 2H, J=4.6Hz) |
| | | | 5.21 | (d, 1H, J=3.9Hz) |
| | | | 5.66 | (d, 1H, J=3.7Hz) |
| | | | 7.32 | (2d, 2H, J=9.2Hz) |
| | | | 8.22 | (2d, 2H, J=9.3Hz) |
| 9 | 3400, 1020 | (OH) | 0.89 | (t, 3H, J=7.0Hz) |
| | 2940 | (alkyl) | 1.25~1.40 | (m, 4H) |
| | 1520, 1340, 870 | (p-nitrophenyl) | 1.50~1.65 | (m, 2H) |
| | | | 2.56 | (2t, 2H, J=7.2Hz) |
| | | | 2.59 | (dd, 1H, J=8.1 and 11.9Hz) |
| | | | 2.94 | (dd, 1H, J=~0 and 11.5Hz) |
| | | | 3.20 | (t, 1H, J=9.2Hz) |
| | | | 4.11 | (t, 1H, J=9.1Hz) |
| | | | 5.09 | (d, 1H, J=3.7Hz) |
| | | | 5.13, 5.14 | (2d, 2H, J=4.4Hz) |
| | | | 5.21 | (d, 1H, J=3.7Hz) |
| | | | 5.67 | (d, 1H, J=3.7Hz) |
| | | | 7.32 | (2d, 2H, J=9.3Hz) |
| | | | 8.22 | (2d, 2H, J=9.3Hz) |
| 10 | 3400, 1020 | (OH) | 0.87 | (t, 3H, J=6.6Hz) |
| | 2940 | (alkyl) | 1.29~1.42 | (m, 6H) |
| | 1520, 1340, 870 | (p-nitrophenyl) | 1.51~1.66 | (m, 2H) |
| | | | 2.46~2.59 | (m, 3H) |

TABLE 2-continued

| Compound No. | IR (KBr) $\nu$cm$^{-1}$ | | $^1$H-NMR (CD$_3$OD): $\delta$ppm | |
|---|---|---|---|---|
| | | | 2.95 | (dd, 1H, J=~0 and 14.3Hz) |
| | | | 3.21 | (t, 1H, J=9.3Hz) |
| | | | 4.12 | (t, 1H, J=9.3Hz) |
| | | | 5.10 | (d, 1H, J=3.7Hz) |
| | | | 5.13, 5.14 | (2d, 2H, J=4.2Hz) |
| | | | 5.22 | (d, 1H, J=3.7Hz) |
| | | | 5.68 | (d, 1H, J=3.5Hz) |
| | | | 7.31 | (2d, 2H, J=9.3Hz) |
| | | | 8.22 | (2d, 2H, J=9.4Hz) |
| 11 | 3400, 1010 | (OH) | 0.90 | (t, 3H, J=6.6Hz) |
| | 2920, 2850 | (CH$_3$CH$_2$) | 1.25~1.37 | (m, 8H) |
| | 1520, 1340, 850 | (p-nitrophenyl) | 1.53~1.56 | (m, 2H) |
| | | | 2.57 | (2t, 2H, J=7.2Hz) |
| | | | 2.60 | (dd, 1H, J=8.0 and 12.5Hz) |
| | | | 2.95 | (dd, 1H, J=~0 and 12.0Hz) |
| | | | 3.21 | (t, 1H, J=9.4Hz) |
| | | | 4.12 | (t, 1H, J=9.0Hz) |
| | | | 5.08 | (d, 1H, J=3.7Hz) |
| | | | 5.12, 5.13 | (2d, 2H, J=4.2Hz) |
| | | | 5.20 | (d, 1H, J=3.7Hz) |
| | | | 5.66 | (d, 1H, J=3.5Hz) |
| | | | 7.32 | (2d, 2H, J=9.4Hz) |
| | | | 8.22 | (2d, 2H, J=9.4Hz) |
| 12 | 3400, 1010 | (OH) | 0.94 | (t, 3H, J=7.7Hz) |
| | 2940, 2860 | (CH$_3$CH$_2$) | 1.24~1.41 | (m, 18H) |
| | 1520, 1350, 860 | (p-nitrophenyl) | 1.51~1.60 | (m, 2H) |
| | | | 2.57 | (2t, 2H, J=7.2Hz) |
| | | | 2.60 | (dd, 1H, J=8.2 and 12.5Hz) |
| | | | 2.95 | (dd, 1H, J=~0 and 12.0Hz) |
| | | | 3.21 | (t, 1H, J=9.2Hz) |
| | | | 4.11 | (t, 1H, J=8.6Hz) |
| | | | 5.08 | (d, 1H, J=3.9Hz) |
| | | | 5.11, 5.12 | (2d, 2H, J=3.9Hz) |
| | | | 5.19 | (d, 1H, J=3.7Hz) |
| | | | 5.66 | (d, 1H, J=3.7Hz) |
| | | | 7.31 | (2d, 2H, J=9.3Hz) |
| | | | 8.22 | (2d, 2H, J=9.3Hz) |
| 13 | 3400, 1010 | (OH) | 0.89 | (t, 3H, J=7.0Hz) |
| | 2950, 2800 | (CH$_3$CH$_2$) | 1.28 | (broad, s, 3OH) |
| | 1520, 1350, 850 | (p-nitrophenyl) | 1.51~1.61 | (m, 2H) |
| | | | 2.57 | (t, 2H, J=7.2Hz) |
| | | | 2.60 | (dd, 1H, J=7.9 and 12.5Hz) |
| | | | 2.95 | (dd, 1H, J=~0 and 13.0Hz) |
| | | | 3.20 | (t, 1H, J=9.3Hz) |
| | | | 4.10 | (t, 1H, J=9.3Hz) |
| | | | 5.09 | (d, 1H, J=3.5Hz) |
| | | | 5.12, 5.14 | (2d, 2H, J=4.1Hz) |
| | | | 5.20 | (d, 1H, J=3.9Hz) |
| | | | 5.66 | (d, 1H, J=3.9Hz) |
| | | | 7.31 | (2d, 2H, J=9.3Hz) |
| | | | 8.22 | (2d, 2H, J=9.3Hz) |
| 14 | 3400, 1020 | (OH) | 1.23 | (2d, 6H, J=6.6Hz) |
| | 2950 | (alkyl) | 2.62 | (dd, 1H, J=8.1 and 11.8Hz) |
| | 1520, 1350, 880 | (p-nitrophenyl) | 2.96~3.08 | (m, 2H) |
| | | | 3.20 | (t, 1H, J=9.3Hz) |
| | | | 4.12 | (t, 1H, J=9.0Hz) |
| | | | 5.09 | (d, 1H, J=3.7Hz) |
| | | | 5.14, 5.15 | (2d, 2H, J=4.2Hz) |
| | | | 5.22 | (d, 1H, J=3.7Hz) |
| | | | 5.67 | (d, 1H, J=3.7Hz) |
| | | | 7.32 | (2d, 2H, J=9.2Hz) |
| | | | 8.22 | (2d, 2H, J=9.2Hz) |
| 15 | 3400, 1020 | (OH) | 0.96 | (2d, 6H, J=6.6Hz) |
| | 2950 | (alkyl) | 1.77 | (m, 1H) |
| | 1520, 1350, 880 | (p-nitrophenyl) | 2.46 | (2d, 2H, J=7.3Hz) |
| | | | 2.57 | (dd, 1H, J=7.9 and 11.6Hz) |
| | | | 2.94 | (dd, 1H, J=2.4 and 13.9Hz) |
| | | | 3.21 | (t, 1H, J=9.2Hz) |
| | | | 4.12 | (t, 1H, J=9.0Hz) |
| | | | 5.10 | (d, 1H, J=3.7Hz) |
| | | | 5.13, 5.15 | (2d, 2H, J=3.9Hz) |
| | | | 5.21 | (d, 1H, J=4.0Hz) |
| | | | 5.66 | (d, 1H, J=3.7Hz) |
| | | | 7.32 | (2d, 2H, J=9.5Hz) |
| | | | 8.22 | (2d, 2H, J=9.2Hz) |
| 16 I S | 3400, 1010 2950 1520, 1350, 870 | (OH) (alkyl) (p-nitrophenyl) | 0.956 1.22 1.40~1.59 2.61 | (t, 3H, J=7.3Hz) (d, 3H, J=7.0Hz) (m, 2H) (dd, 1H, J=7.9 and 11.3Hz) |

TABLE 2-continued

| Compound No. | IR (KBr) $\nu$cm$^{-1}$ | | $^1$H-NMR (CD$_3$OD): $\delta$ppm | |
|---|---|---|---|---|
| form | | | 2.73~2.83 | (m, 1H) |
| | | | 2.97 | (dd, 1H, J=1.8 and 13.8Hz) |
| | | | 3.200 | (t, 1H, J=9.3Hz) |
| | | | 4.12 | (t, 1H, J=9.0Hz) |
| | | | 5.10 | (d, 1H, J=3.5Hz) |
| | | | 5.11, 5.15 | (2d, 2H, J=3.8Hz) |
| | | | 5.22 | (d, 1H, J=3.7Hz) |
| | | | 5.67 | (d, 1H, J=3.7Hz) |
| | | | 7.32 | (2d, 2H, J=9.5Hz) |
| | | | 8.22 | (2d, 2H, J=9.2Hz) |
| 16 | 3400, 1010 | (OH) | 0.952 | (t, 3H, J=7.5Hz) |
| II | 2950 | (alkyl) | 1.22 | (d, 3H, J=7.0Hz) |
| R | 1520, 1350, 870 | (p-nitrophenyl) | 1.50~1.69 | (m, 2H) |
| form | | | 2.61 | (dd, 1H, J=7.9 and 11.3Hz) |
| | | | 2.72~2.82 | (m, 1H) |
| | | | 2.97 | (dd, 1H, J=1.8 and 13.8Hz) |
| | | | 3.212 | (t, 1H, J=9.2Hz) |
| | | | 4.12 | (t, 1H, J=9.0Hz) |
| | | | 5.10 | (d, 1H, J=3.5Hz) |
| | | | 5.11, 5.15 | (2d, 2H, J=3.8Hz) |
| | | | 5.22 | (d, 1H, J=3.7Hz) |
| | | | 5.67 | (d, 1H, J=3.7Hz) |
| | | | 7.32 | (2d, 2H, J=9.5Hz) |
| | | | 8.22 | (2d, 2H, J=9.2Hz) |
| 17 | 3400, 1020 | (OH) | 0.88 | (2d, 6H, J=6.7Hz) |
| | 2950 | (alkyl) | 1.35~1.48 | (m, 2H) |
| | 1520, 1350, 880 | (p-nitrophenyl) | 1.58~1.70 | (m, 1H) |
| | | | 2.55~2.64 | (m, 3H) |
| | | | 2.95 | (dd, 1H, J=2.0 and 13.8Hz) |
| | | | 3.21 | (t, 1H, J=9.3Hz) |
| | | | 4.12 | (t, 1H, J=9.0Hz) |
| | | | 5.09 | (d, 1H, J=4.0Hz) |
| | | | 5.13, 5.15 | (2d, 2H, J=3.8Hz) |
| | | | 5.21 | (d, 1H, J=3.7Hz) |
| | | | 5.67 | (d, 1H, J=3.7Hz) |
| | | | 7.32 | (2d, 2H, J=9.2Hz) |
| | | | 8.22 | (2d, 2H, J=9.2Hz) |
| 18 | 3400, 1020 | (OH) | 1.26 | (t, 6H, J-7.2Hz) |
| | 2920 | (CH$_3$CH$_2$) | 2.71 | (dd, 1H, J=7.4 and 12.5Hz) |
| | 1400 | {(CH$_3$CH$_2$)$_2$NCH$_2$CH$_2$S} | 2.91 | (m, 2H) |
| | 1520, 1350, 870 | (p-nitrophenyl) | 3.02 | (dd, 1H, J=~0 and 12.5Hz) |
| | | | 3.12 | (2dd, 2H, J=12.6 and 7.2Hz) |
| | | | 3.21~3.27 | (m, 3H) |
| | | | 4.10 | (t, 1H, J=9.0Hz) |
| | | | 5.13~5.15 | (3d, 3H) |
| | | | 5.20 | (d, 1H, J=3.9Hz) |
| | | | 5.66 | (d, 1H, J=3.7Hz) |
| | | | 7.31 | (2d, 2H, J=9.4Hz) |
| | | | 8.22 | (2d, 2H, J=9.2Hz) |
| 19 | 3400, 1020 | (OH) | 2.67 | (dd, 1H, J=8.0 and 12.3Hz) |
| | 2920 | (CH$_3$CH$_2$) | 2.72 | (s, 6H) |
| | 1400 | {(CH$_3$)$_2$NCH$_2$CH$_2$S} | 2.91 | (m, 2H) |
| | 1510, 1350, 870 | (p-nitrophenyl) | 3.06 | (dd, 1H, J=~0 and 12.3Hz) |
| | | | 3.15 | (m, 2H) |
| | | | 3.22 | (t, 1H, J=9.3Hz) |
| | | | 4.11 | (t, 1H, J=9.1Hz) |
| | | | 5.15~5.16 | (3d, 3H) |
| | | | 5.22 | (d, 1H, J=3.9Hz) |
| | | | 5.67 | (d, 1H, J=3.7Hz) |
| | | | 7.32 | (2d, 2H, J=9.3Hz) |
| | | | 8.21 | (2d, 2H, J=9.3Hz) |
| 20 | 3400, 1030 | (OH) | 2.65 | (m, 3H) |
| | 2930 | (CH$_3$, CH$_2$) | 2.76 | (s, 6H) |
| | 1410 | {(CH$_3$)$_2$NCH$_2$CH$_2$CH$_2$S} | 2.98 | (dd, 1H, J=~0 and 12.3Hz) |
| | 1520, 1350, 850 | (p-nitrophenyl) | 3.07 | (m, 2H) |
| | | | 3.22 | (t, 1H, J=9.0Hz) |
| | | | 3.25 | (m, 2H) |
| | | | 4.11 | (t, 1H, J=9.1Hz) |
| | | | 5.10 | (d, 1H, J=3.7Hz) |
| | | | 5.14, 5.16 | (2d, 2H, J=3.9Hz) |
| | | | 5.22 | (d, 1H, J=3.9Hz) |
| | | | 5.67 | (d, 1H, J=3.7Hz) |
| | | | 7.32 | (2d, 2H, J=9.2Hz) |
| | | | 8.22 | (2d, 2H, J=9.3Hz) |
| 21 | 3300, 1020 | (OH) | 1.62~1.69 | (m, 2H) |
| | 2950 | (CH$_2$) | 1.78~1.87 | (m, 4H) |
| | 1520, 1350, 850 | (p-OPhNO$_2$) | 2.72 | (dd, 1H, J=7.3 and 12.3Hz) |
| | 1400 | (NCH$_2$) | 2.93~3.00 | (m, 2H) |
| | | | 3.03 | (dd, 1H, J=1.8 and 12.5Hz) |

TABLE 2-continued

| Compound No. | IR (KBr) $\nu\text{cm}^{-1}$ | | $^1$H-NMR (CD$_3$OD): δppm | |
|---|---|---|---|---|
| | | | 3.14~3.29 | (m, 7H) |
| | | | 4.12 | (t, 1H, J=8.9Hz) |
| | | | 5.14~5.17 | (3d, 3H) |
| | | | 5.22 | (d, 1H, J=3.9Hz) |
| | | | 5.67 | (d, 1H, J=3.7Hz) |
| | | | 7.32 | (2d, 2H, J=9.2Hz) |
| | | | 8.23 | (2d, 2H, J=9.2Hz) |
| 22 | 3300, 1020 | (OH) | 1.67~1.68 | (m, 2H) |
| | 2950 | (CH$_2$) | 1.84~1.93 | (m, 4H) |
| | 1520, 1350, 860 | (p-OPhNO$_2$) | 2.01~2.07 | (m, 2H) |
| | 1400 | (NCH$_2$) | 2.63~2.72 | (m, 3H) |
| | | | 2.99 | (dd, 1H, J=~0 and 12.1Hz) |
| | | | 2.14~3.26 | (m, 7H) |
| | | | 4.11 | (t, 1H, J=8.8Hz) |
| | | | 5.10 | (d, 1H, J=3.5Hz) |
| | | | 5.12, 5.15 | (2d, 2H, J=3.4Hz) |
| | | | 5.21 | (d, 1H, J=4.0Hz) |
| | | | 5.67 | (d, 1H, J=3.7Hz) |
| | | | 7.33 | (2d, 2H, J=9.2Hz) |
| | | | 8.22 | (2d, 2H, J=9.4Hz) |
| 23 | 3400, 1030 | (OH) | 2.58~2.71 | (m, 9H) |
| | 2940 | (CH$_2$) | 3.00 | (dd, 1H, J=~0 and 12.3Hz) |
| | 1520, 1350, 850 | (p-nitrophenyl) | 3.23 | (t, 1H, J=9.3Hz) |
| | 1400 | (NCH$_2$) | 4.12 | (t, 1H, J=9.0Hz) |
| | | | 5.11 | (d, 1H, J=3.7Hz) |
| | | | 5.14, 5.16 | (2d, 2H, J=4.0Hz) |
| | | | 5.22 | (d, 1H, J=3.7Hz) |
| | | | 5.68 | (d, 1H, J=3.7Hz) |
| | | | 7.32 | (2d, 2H, J=9.3Hz) |
| | | | 8.22 | (2d, 2H, J=9.3Hz) |
| 24 | 3400, 1030 | (OH) | 1.77~1.83 | (m, 2H) |
| | 3010 | (NH) | 2.59 | (dd, 1H, J=7.8 and 13.6Hz) |
| | 2940 | (CH$_2$) | 2.61~2.69 | (m, 8H) |
| | 1520, 1350, 860 | (p-OPhNO$_2$) | 2.98 | (dd, 1H, J=~0 and 12.3Hz) |
| | 1400 | (NCH$_2$) | 3.19~3.25 | (m, 5H) |
| | | | 4.13 | (t, 1H, J=8.4Hz) |
| | | | 5.14~5.21 | (3d, 3H) |
| | | | 5.25 | (d, 1H, J=3.7Hz) |
| | | | 5.71 | (d, 1H, J=3.5Hz) |
| | | | 7.33 | (2d, 2H, J=9.4Hz) |
| | | | 8.24 | (2d, 2H, J=9.3Hz) |
| 25 | 3400, 1030 | (OH) | 2.60 | (dd, 1H, J=7.6 and 12.4Hz) |
| | 2940 | (CH$_2$) | 2.92 | (dd, 1H, J=2.5 and 14.1Hz) |
| | 1570, 1400, 750, 710 | (picolyl) | 3.21 | (t, 1H, J=9.1Hz) |
| | 1520, 1350, 860 | (p-OPhNO$_2$) | 4.11 | (t, 1H, J=9.1Hz) |
| | | | 5.09 | (d, 1H, J=3.7Hz) |
| | | | 5.14, 5.15 | (2d, 2H, J=3.8Hz) |
| | | | 5.21 | (d, 1H, J=3.5Hz) |
| | | | 5.66 | (d, 1H, J=3.7Hz) |
| | | | 7.25~7.27 | (m, 1H) |
| | | | 7.31 | (2d, 2H, J=9.3Hz) |
| | | | 7.48 | (d, 1H, J=7.9Hz) |
| | | | 7.78 | (dt, 1H, J=1.8 and 7.7Hz) |
| | | | 8.21 | (2d, 2H, J=9.3Hz) |
| | | | 8.43 | (d, 1H, J=3.9Hz) |
| 26 | 3400, 1020 | (OH) | 2.54 | (dd, 1H, J=7.4 and 12.3Hz) |
| | 2930 | (CH) | 2.84 | (dd, 1H, J=2.2 and 12.3Hz) |
| | 1520, 1350 | (NO$_2$) | 3.26 | (t, 1H, J=8.8Hz) |
| | 860, 750, 710 | (phenyl) | 4.11 | (t, 1H, J=8.8Hz) |
| | | | 5.12~5.17 | (3d, 3H, J=3.7, 3.8, 4.0Hz) |
| | | | 5.21 | (d, 1H, J=4.0Hz) |
| | | | 5.66 | (d, 1H, J=3.7Hz) |
| | | | 7.31 | (2d, 2H, J=9.3Hz) |
| | | | 7.34~7.39 | (m, 1H) |
| | | | 7.84 | (~d, 1H, J=7.9Hz) |
| | | | 8.21 | (2d, 2H, J=9.4Hz) |
| | | | 8.38 | (~d, 1H, J=4.4Hz) |
| | | | 8.48 | (~s, 1H) |
| 27 | 3300, 1020 | (OH) | 2.54 | (dd, 1H, J=7.1 and 12.4Hz) |
| | 2930 | (CH$_2$) | 2.83 | (dd, 1H, J=~0 and 12.4Hz) |
| | 1520, 1350 | (NO$_2$) | 3.22 | (t, 1H, J=9.3Hz) |
| | 860, 750, 710 | (phenyl) | 4.11 | (t, 1H, J=8.8Hz) |
| | | | 5.11~5.16 | (3d, 3H, J=3.7, 3.8, 3.9Hz) |
| | | | 5.21 | (d, 1H, J=3.9Hz) |
| | | | 5.66 | (d, 1H, J=3.5Hz) |
| | | | 7.31 | (2d, 2H, J=9.2Hz) |
| | | | 7.42 | (~d, 1H, J=5.9Hz) |
| | | | 8.21 | (2d, 2H, J=9.3Hz) |
| | | | 8.43 | (~d, 1H, J=5.7Hz) |

TABLE 2-continued

| Compound No. | IR (KBr) νcm$^{-1}$ | | $^1$H-NMR (CD$_3$OD): δppm | |
|---|---|---|---|---|
| 28 | 3400, 1010 | (OH) | 2.51 | (dd, 1H, J=7.4 and 14.4Hz) |
| | 2930 | (CH) | 2.80 | (dd, 1H, J=~0 and 14.3Hz) |
| | 1520, 1350 | (NO$_2$) | 3.20 | (t, 1H, J=9.3Hz) |
| | 870, 710 | (phenyl) | 4.08 | (t, 1H, J=8.1Hz) |
| | | | 4.13 | (s, 2H) |
| | | | 5.07 | (d, 1H, J=3.7Hz) |
| | | | 5.13, 5.15 | (2d, 2H, J=3.8 and 3.9Hz) |
| | | | 5.20 | (d, 1H, J=3.9Hz) |
| | | | 5.65 | (d, 1H, J=3.5Hz) |
| | | | 7.31 | (2d, 2H, J=9.3Hz) |
| | | | 7.44 | (~dt, 1H, J=2.2 and 7.7Hz) |
| | | | 7.53 | (dd, 1H, J=1.8 and 7.7Hz) |
| | | | 7.58 | (dt, 1H, J=1.5 and 7.7Hz) |
| | | | 7.93 | (dd, 1H, J=1.1 and 8.0Hz) |
| | | | 8.21 | (2d, 2H) |
| 29 | 3400, 1030 | (OH) | 2.06 | (broad s, 4H) |
| | 2930 | (CH) | 2.75 | (dd, 1H, J=7.4 and 14.2Hz) |
| | 1520, 1350 | (NO$_2$) | 2.92~2.97 | (m, 2H) |
| | 1410 | (NCH$_2$) | 3.07 | (dd, 1H, J=~0 and 14.3Hz) |
| | 870 | (phenyl) | 3.21~3.39 | (m, 7H) |
| | | | 4.15 | (t, 1H, J=9.1Hz) |
| | | | 5.22~5.23 | (3d, 3H) |
| | | | 5.29 | (d, 1H, J=3.9Hz) |
| | | | 5.74 | (d, 1H, J=3.7Hz) |
| | | | 7.32 | (2d, 2H, J=9.3Hz) |
| | | | 8.21 | (2d, 2H, J=9.3Hz) |
| 30 | 3400, 1020 | (OH) | 1.87 | (p, 2H, J=7.4Hz) |
| | 2930 | (CH) | 2.57 | (t, 2H, J=7.2Hz) |
| | 1510, 1340 | (NO$_2$) | 2.65 | (~dd, 2H, J=7.4 and 13.5Hz) |
| | 850, 700 | (phenyl) | 2.95 | (dd, 1H, J=~0 and 11.9Hz) |
| | | | 3.20 | (t, 1H, J=9.3Hz) |
| | | | 4.12 | (t, 1H, J=9.0Hz) |
| | | | 5.06 | (d, 1H, J=3.7Hz) |
| | | | 5.12, 5.14 | (2d, 2H, J=3.7 and 3.9Hz) |
| | | | 5.21 | (d, 1H, J=3.7Hz) |
| | | | 5.67 | (d, 1H, J=3.7Hz) |
| | | | 7.10~7.26 | (m, 5H) |
| | | | 7.31 | (2d, 2H, J=9.3Hz) |
| | | | 8.20 | (2d, 2H, J=9.2Hz) |
| 31 | 3400, 1020 | (OH) | 2.14 | (s, 3H) |
| | 3030 | (CH$_3$) | 2.61 | (dd, 1H, J=7.8 and 14.2Hz) |
| | 1520, 1340 | (NO$_2$) | 2.93 | (dd, 1H, J=2.2 and 14.1Hz) |
| | 850 | (phenyl) | 3.23 | (t, 1H, J=9.3Hz) |
| | | | 4.12 | (t, 1H, J=8.9Hz) |
| | | | 5.12 | (d, 1H, J=3.7Hz) |
| | | | 5.14~5.17 | (2d, 2H, J=4.0 and 4.2Hz) |
| | | | 5.23 | (d, 1H, J=3.9Hz) |
| | | | 5.69 | (d, 1H, J=3.7Hz) |
| | | | 7.33 | (2d, 2H, J=9.3Hz) |
| | | | 8.23 | (2d, 2H) |
| 32 | 3400 | (OH) | 2.52 | (dd, 1H, J=7.7 and 12.0Hz) |
| | 2920 | (CH) | 2.86 | (dd, 1H, J=~0 and 12.3Hz) |
| | 1520, 1380 | (NO$_2$) | 3.22 | (t, 1H, J=9.3Hz) |
| | 850, 700 | (phenyl) | 4.20 | (t, 1H, J=8.8Hz) |
| | | | 5.15, 5.20 | (2d, 2H, J=3.5 and 3.7Hz) |
| | | | 5.83 | (d, 1H, J=3.3Hz) |
| | | | 7.13~7.32 | (m, 5H) |
| | | | 7.50 | (d, 1H, J=9.3Hz) |
| | | | 8.17 | (dd, 1H, J=2.7 and 9.4Hz) |
| | | | 8.28 | (d, 1H, J=2.8Hz) |
| 33 | 3400 | (OH) | 2.52 | (dd, 1H, J=7.6 and 12.0Hz) |
| | 2900 | (CH) | 2.85 | (dd, 1H, J=~0 and 12.3Hz) |
| | 1520, 1380 | (NO$_2$) | 3.21 | (t, 1H, J=9.3Hz) |
| | 850, 700 | (phenyl) | 4.19 | (t, 1H, J=8.7Hz) |
| | | | 5.13, 5.15, 5.20 | (3d, 3H, J=3.8, 3.8, 3.9Hz) |
| | | | 5.81 | (d, 1H, J=3.5Hz) |
| | | | 7.14~7.33 | (m, 5H) |
| | | | 7.49 | (d, 1H, J=9.2Hz) |
| | | | 8.17 | (dd, 1H, J=2.6 and 9.2Hz) |
| | | | 8.29 | (d, 1H, J=2.7Hz) |
| 34 | 3300 | (OH) | 2.52 | (dd, 1H, J=7.7 and 14.3Hz) |
| | 2940 | (CH) | 2.86 | (dd, 1H, J=2.4 and 14.5Hz) |
| | 1530, 1360 | (NO$_2$) | 3.21 | (t, 1H, J=9.2Hz) |
| | 860, 710 | (phenyl) | 4.18 | (t, 1H, J=9.1Hz) |
| | | | 5.12, 5.14, 5.16 | (3d, 3H, J=3.7, 3.7, 3.7Hz) |
| | | | 5.20 | (d, 1H, J=4.0Hz) |
| | | | 5.82 | (d, 1H, J=3.5Hz) |
| | | | 7.15~7.35 | (m, 5H) |
| | | | 7.50 | (d, 1H, J=9.3Hz) |

TABLE 2-continued

| Compound No. | IR (KBr) νcm⁻¹ | ¹H-NMR (CD₃OD): δppm |
|---|---|---|
| | 8.18 | (dd, 1H, J=2.8 and 9.3Hz) |
| | 8.32 | (d, 1H, J=2.8Hz) |

EXAMPLE 35

Synthesis of sulfoxide form of Compound No. 1 (Compound No. 35) of the formula:

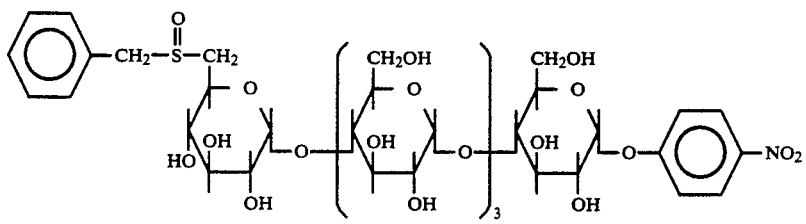

Compound No. 1 in an amount of 0.057 mmol was dissolved in acetic acid, cooled at 0° C. in the dark, and added with 0.057 mmol of m-chloroperbenzoic acid in the dark, followed by stirring at 25° C. for reaction. The end of the reaction was confirmed by TLC (butanol:ethanol:water=4:2:1 v/v/v), followed by extraction of the reaction solution with water. After washing the aqueous layer with dichloromethane under acidic conditions, it was concentrated under reduced pressure to give 67 mg of a mixture comprising unreacted Compound No. 1, Compound No. 35-I (R form), Compound No. 35-II (S form) (two isomers of Compound No. 35), and a sulfone form of Compound No. 1. The mixture was subjected to HPLC (high performance chromatography) to obtain 13.2 mg of Compound No. 35-I (R form) and 12.1 mg of Compound No. 35-II (S form).

Yield: R form: 22%, S form 20%

[α]: R form +188° (CH₃OH), S form +167° (CH₂OH)

IR and ¹H-NMR: See Table 3

EXAMPLE 36

Synthesis of sulfoxide form of Compound No. 2 (Compound No. 36)

The process of Example 35 was repeated except of using Compound No. 2 in place of compound No. 1 to synthesize Compound No. 36-I (R form) and Compound No. 36-II (S form).

Yield: R form 14%, S form 11%

EXAMPLE 37

Synthesis of sulfoxide form of Compound No. 10 (Compound No. 37)

The process of Example 35 was repeated except for using Compound No. 10 in place of Compound No. 1 to synthesize Compound No. 37-I (R form) and Compound No. 36-II (S form).

Yield: R form 25%, S form 21%

[α]$_D$: R form +138° (CH₃OH), S form +150° (CH₃OH)

¹H-NMR: See Table 4.

TABLE 3

| Compound No. | IR(KBr)νcm⁻¹ | | ¹H-NMR(CD₃OD): δppm | |
|---|---|---|---|---|
| 35 | 3400, 1020 | (OH) | 2.88 | (dd, 1H, J=7.3 and 12.2Hz) |
| I | 2940 | (CH₂) | 4.08 | (dt, 1H, J=7.8 and 2.0Hz) |
| | 1520, 1340, 860 | (p-nitrophenyl) | 4.10 | (t, 1H, J=8.1Hz) |
| R | 1030 | (SO) | 4.09, 4.25 | (2d, 2H, J=13.2Hz) |
| form | 700 | (phenyl) | 5.13, 5.14 | (2d, 2H, J=4.4Hz) |
| | | | 5.21 | (d, 1H, J=3.8Hz) |
| | | | 5.24 | (d, 1H, J=3.5Hz) |
| | | | 5.66 | (d, 1H, J=3.7Hz) |
| | | | 7.31 | (2d, 2H, J=9.4Hz) |
| | | | 7.30~7.35 | (m, 5H) |
| | | | 8.22 | (2d, 2H, J=9.3Hz) |
| 35 | 3400, 1020 | (OH) | 2.86 | (dd, 1H, J=10.9 and 13.2Hz) |
| II | 2940 | (CH₂) | 3.13 | (t, 1H, J=9.4Hz) |
| | 1520, 1340, 860 | (p-nitrophenyl) | 3.20 | (dd, 1H, J=1.7 and 13.2Hz) |
| S | 1050 | (SO) | 4.02, 4.10 | (2d, 2H, J=13.2Hz) |
| form | 700 | (phenyl) | 4.06 | (dt, 1H, J=11.5 and 1.7Hz) |
| | | | 4.10 | (t, 1H, J=9.2Hz) |
| | | | 5.10, 5.13 | (2d, 2H, J=3.7 and 3.8H) |
| | | | 5.18 | (d, 1H, J=3.8Hz) |
| | | | 5.21 | (d, 1H, J=3.7Hz) |
| | | | 5.67 | (d, 1H, J=3.5Hz) |
| | | | 7.32 | (2d, 2H, J=9.4Hz) |
| | | | 7.31~7.35 | (m, 5H) |
| | | | 8.22 | (2d, 2H, J=9.2Hz) |

TABLE 4

| Compound No. | | $^1$H-NMR(CD$_3$OD): δppm | |
|---|---|---|---|
| 37 | | 0.90 | (t, 3H, J=7.1Hz) |
| I | | 1.28~1.48 | (m, 6H) |
| | | 1.70~1.77 | (m, 2H) |
| R | | 2.87 | (t, 2H, J=7.5Hz) |
| form | | 2.96 | (dd, 1H, J=7.1 and 11.9Hz) |
| | | 4.05~4.14 | (m, 1H) |
| | | 4.10 | (t, 1H, J=8.5Hz) |
| | | 5.12, 5.14 | (2d, 2H, J=3.9Hz) |
| | | 5.20 | (2d, 2H, J=3.7Hz) |
| | | 5.66 | (d, 1H, J=3.5Hz) |
| | | 7.32 | (2d, 2H, J=9.3Hz) |
| | | 8.22 | (2d, 2H, J=9.3Hz) |
| 37 | | 0.91 | (t, 3H, J=7.1Hz) |
| II | | 1.28~1.51 | (m, 6H) |
| | | 1.70~1.81 | (m, 2H) |
| S | | 2.70~2.89 | (m, 2H) |
| form | | 2.85 | (dd, 1H, J=10.8 and 12.5Hz) |
| | | 3.16 | (t, 1H, J=9.3Hz) |
| | | 3.22 | (dd, 1H, J=~0 and 11.9Hz) |
| | | 4.07 | (m, 1H) |
| | | 4.10 | (t, 1H, J=9.3Hz) |
| | | 5.11, 5.13 | (2d, 2H, J=3.9 and 4.2Hz) |
| | | 5.19, 5.20 | (2d, 2H, J=4.0Hz) |
| | | 5.66 | (d, 1H, J=3.7Hz) |
| | | 7.32 | (2d, 2H, J=9.4Hz) |
| | | 8.22 | (2d, 2H, J=9.3Hz) |

EXAMPLE 38

Synthesis of sulfone form of Compound No. 1

(Compound No. 38) of the formula

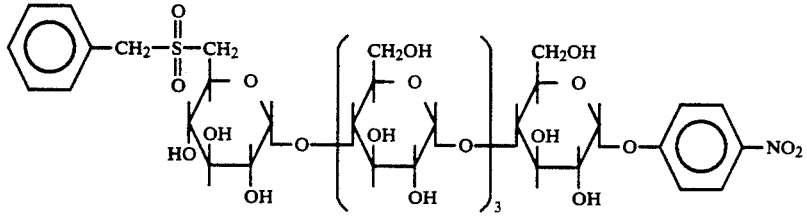

Compound No. 1 in an amount of 0.028 mmol was dissolved in acetic acid, cooled at 0° C. in the dark, and added with 0.085 mmol of m-chloroperbenzoic acid, followed by stirring at 25° C. in the dark. The end of the reaction was confirmed by TLC (butanol:ethanol:water=4:2:1 v/v/v), followed by extraction of the reaction solution with water. The aqueous layer was washed with dichloromethane under acidic conditions and condensed under reduced pressure to give 28.30 mg of the desired compound.

Yield: 43%

$[\alpha]_D$: +169° (CH$_3$OH)

IR and $^1$H-NMR: See Table 5

EXAMPLE 39

Synthesis of sulfone form of Compound No. 2

(Compound No. 39)

The process of Example 38 was repeated except for using Compound No. 2 in place of Compound No. 1 to synthesize Compound No. 39.

Yield: 88%

$[\alpha]_D$: +91° (CH$_3$OH)

IR and $^1$H-NMR: See Table 5

TABLE 5

| Compound No. | IR(KBr)νcm$^{-1}$ | | $^1$H-NMR(CD$_3$OD): δppm | |
|---|---|---|---|---|
| 38 | 3400, 1020 | (OH) | 3.12 | (t, 1H, J=9.4Hz) |
| | 2940 | (CH$_2$) | 4.11 | (t, 1H, J=9.1Hz) |
| | 1520, 1340, 850 | (p-nitrophenyl) | 4.15 | (dt, 1H, J=9.1 and 2.0Hz) |
| | 1300, 1110 | (SO$_2$) | 4.44, 4.55 | (2d, 2H, J=13.9Hz) |
| | 700 | (phenyl) | 5.14, 5.15 | (2d, 2H, J=3.3Hz) |
| | | | 5.21 | (d, 1H, J=3.7Hz) |
| | | | 5.39 | (d, 1H, J=3.3Hz) |
| | | | 5.66 | (d, 1H, J=3.9Hz) |
| | | | 7.32 | (2d, 2H, J=9.3Hz) |
| | | | 7.35~7.46 | (m, 5H) |
| | | | 8.21 | (2d, 2H, J=9.3Hz) |
| 39 | 3400, 1020 | (OH) | 2.34 | (s, 3H) |
| | 2940 | (CH$_3$, CH$_2$) | 3.11 | (t, 1H, J=9.3Hz) |
| | 1520, 1350, 850 | (p-OPhNO$_2$) | 4.11 | (t, 1H, J=8.8Hz) |
| | 1310, 1110 | (SO$_2$) | 4.14 | (dt, 1H, J=2.3 and 8.6Hz) |
| | 700 | (Ph) | 4.38, 4.50 | (2d, 2H, J=14.1Hz) |
| | | | 5.13, 5.15 | (2d, 2H, J=3.5Hz) |
| | | | 5.21 | (d, 1H, J=3.9Hz) |
| | | | 5.37 | (d, 1H, J=3.3Hz) |
| | | | 5.66 | (d, 1H, J=3.7Hz) |
| | | | 7.31 | (2d, 2H, J=9.2Hz) |
| | | | 7.31~7.39 | (m, 4H) |
| | | | 8.22 | (2d, 2H, J=9.3Hz) |

EXAMPLE 40

Synthesis of sulfone form of Compound No. 10

(Compound No. 40)

The process of Example 38 was repeated except for using Compound No. 10 except for using Compound No. 1.

Yield: 13%

$[\alpha]_D$: 156° (CH$_3$OH)

$^1$H-NMR: See Table 6.

TABLE 6

| Compound No. | ¹H-NMR(CD₃OD): δppm | |
|---|---|---|
| 40 | 0.91 | (t, 3H, J=6.6Hz) |
| | 1.28~1.59 | (m, 6H) |
| | 1.73~1.81 | (m, 2H) |
| | 3.13 | (t, 1H, J=9.3Hz) |
| | 3.16~3.23 | (m, 2H) |
| | 4.06~4.13 | (m, 1H) |
| | 4.11 | (t, 1H, J=8.9Hz) |
| | 5.12, 5.14 | (2d, 2H, J=3.7 and 3.5Hz) |
| | 5.21 | (d, 1H, J=3.8Hz) |
| | 5.28 | (d, 1H, J=3.5Hz) |
| | 5.66 | (d, 1H, J=3.5Hz) |
| | 7.32 | (2d, 2H, J=9.4Hz) |
| | 8.22 | (2d, 2H, J=9.3Hz) |

EXAMPLE 41

Synthesis of p-nitrophenyl O-[6-S-{(2-morpholino)ethyl}-6-thio-α-D-glucopyranosyl]-(1→4)-tris}O-α-D-glucopyranosyl-(1→4)}-α-D-glucopyranoside (Compound No. 23)

Tosyl chloride in an amount of 236 mg (1.24 mmol) was dissolved in dichloromethane, cooled at 0° C., and added with 0.1 ml (0.825 mmol) of 4-(2-hydroxyl)-morpholine and 0.07 ml (0.825 mmol) of pyridine, followed by stirring at 5° C. overnight. The end of the reaction was confirmed by TLC (dichloromethane:methanol=20:1 v/v), followed by extraction of the reaction solution with 2N HCl. The 2N HCl layer was washed with dichloromethane, and the extract was made alkaline with Na₂CO₃, followed by extraction with dichloromethane. The extract was dried over anhydrous sodium sulfate and concentrated at 25° C. under reduced pressure to give a mixture of a compound of the formula: $R^2OR_S$ (wherein $R^2$ is a morpholinoethyl group; and $R_S$ is a tosyl group) and pyridine.

On the other hand, Fullacetyl-AcSG5P obtained in the same manner as described in Example 1(1) in an amount of 289.2 mg (0.176 mmol) was dissolved in 30 ml of methanol, cooled at 0° C. and added with 0.12 ml of methanol solution containing sodium methoxide (containing 0.176 mmol of sodium methoxide), followed by stirring at 0° C. for 30 minutes. To this, the above-mentioned mixture freshly prepared containing the compound of the formula: $R^2OR_S$ and pyridine was added and stirred at 5° C. for 20 hours under a nitrogen stream. The end of the reaction was confirmed by TLC (acetone:acetic acid:H₂O=5:1:1 v/v/v), double development) and the reaction solution was neutralized using an ion exchange resin (Amberlite IR-120(H⁺)) After removing the resin by filtration, followed by washing with methanol, the filtrate and washed solution were combined and concentrated at 30° C. under reduced pressure. The resulting residue was subjected to column chromatography [Sephadex LH-20 (Pharmacia LKB Biotechnology); eluent:methanol, sep-pak (plus ENV,C₁₈, mfd. by Waters Co.); eluents: (a) water, (b) water:methanol=10:2 v/v] to obtain Compound No. 23 (159 mg).

Yield: 84%

$[\alpha]_D$: +155° (C=0.41, CH₃OH)

IR and ¹H-NMR: The same as the results of Example 23

EXAMPLES 42 TO 44

Synthesis of various oligosaccharide derivatives of the formula [II] shown in Tables 7 and 8

The process of Example 41 was repeated except for changing starting compounds to give the compounds shown in Table 7.

The yields and $[\alpha]_D$ of the resulting Compound Nos. 42 to 44 are shown in Table 7 and IR and ¹H-NMR data are shown in Table 8.

TABLE 7

| Compound No. | Compound of Formula [II] | | n | Yield % | $[\alpha]_D$ (CH₃OH) |
|---|---|---|---|---|---|
| | R² | R¹ | | | |
| 42 | —CH₂—CH₂—N(morpholino) | Cl-phenyl-NO₂ | 1 | 19 | +136° |
| 43 | " | " | 2 | 35 | +134° |
| 44 | " | " | 3 | 32 | +121° |

TABLE 8

| Compound No. | IR(KBr)νcm⁻¹ | | ¹H-NMR(CD₃OD): δppm | |
|---|---|---|---|---|
| 42 | 3300 | (OH) | 2.48~2.51 | (m, 4H) |
| | 2920 | (CH) | 2.57~2.77 | (m, 5H) |
| | 1520, 1350 | (NO₂) | 3.00 | (dd, 1H, J=2.0 and 14.3Hz) |
| | 860 | (phenyl) | 3.22 | (t, 1H, J=9.3Hz) |
| | | | 4.19 | (t, 1H, J=9.2Hz) |
| | | | 5.12 | (2d, 2H, J=4.0Hz) |
| | | | 5.19 | (2d, 2H, J=3.7Hz) |
| | | | 5.82 | (d, 1H, J=3.7Hz) |
| | | | 7.50 | (d, 1H, J=9.2Hz) |
| | | | 8.18 | (dd, 1H, J=2.7 and 9.2Hz) |
| | | | 8.32 | (d, 1H, J=2.8Hz) |
| 43 | 3400 | (OH) | 2.47~2.50 | (m, 4H) |
| | 2940 | (CH) | 2.56~2.78 | (m, 5H) |

TABLE 8-continued

| Compound No. | IR(KBr)νcm$^{-1}$ | | $^1$H-NMR(CD$_3$OD): δppm | |
|---|---|---|---|---|
| | 1520, 1350 | (NO$_2$) | 2.99 | (dd, 1H, J=2.2 and 14.1Hz) |
| | 860 | (phenyl) | 3.22 | (t, 1H, J=9.2Hz) |
| | | | 4.19 | (t, 1H, J=9.1Hz) |
| | | | 5.10, 5.15, 5.19 | (3d, 3H, J=3.5, 3.7, 3.8Hz) |
| | | | 5.82 | (d, 1H, J=3.7Hz) |
| | | | 7.50 | (d, 1H, J=9.3Hz) |
| | | | 8.18 | (dd, 1H, J=2.8 and 9.2Hz) |
| | | | 8.32 | (d, 1H, J=2.8Hz) |
| 44 | 3300 | (OH) | 2.45~2.56 | (m, 4H) |
| | 2960 | (CH) | 2.48, 2.75 | (2m, 4H) |
| | 1520, 1360 | (NO$_2$) | 2.67 | (dd, 1H, J=6.8 and 14.8Hz) |
| | 870 | (phenyl) | 3.00 | (dd, 1H, J=2.3 and 14.3Hz) |
| | | | 3.22 | (t, 1H, J=9.3Hz) |
| | | | 4.19 | (t, 1H, J=9.3Hz) |
| | | | 5.10 | (d, 1H, J=3.7Hz) |
| | | | 5.14, 5.15 | (2d, 2H, J=4.2 and 4.3Hz) |
| | | | 5.20 | (d, 1H, J=3.9Hz) |
| | | | 5.82 | (d, 1H, J=3.7Hz) |
| | | | 7.51 | (d, 1H, J=9.2Hz) |
| | | | 8.18 | (dd, 1H, J=2.7 and 9.4Hz) |
| | | | 8.33 | (d, 1H, J=2.7Hz) |

EXAMPLE 45

Measurement of hydrolysis rate and Km value by α-amylase using various oligosaccharide derivatives as substrate

Procedure

Using various oligosaccharide derivatives as shown in Table 9 as a substrate, Km values (mM) and hydrolysis rates (Vmax) in 50 mM BES [N,N-bis(2-hydroxyethyl)-2-aminoethanesulfonic acid]-NaOH buffer solution (pH 7.6, containing 20 mM NaCl and 2 mM CaCl$_2$) were obtained according to a conventional method.

Results

The results are shown in Table 9. The hydrolysis rate is shown in terms of a relative value by taking the hydrolysis rate of (p-nitrophenyl)-maltopentaoside (G5P) as 1.

EXAMPLE 46

Search for hydrolyzed position by α-amylase using various oligosaccharide derivatives as substrate Using the same oligosaccharide derivatives as used in Example 45, hydrolyzed positions were searched.

Procedure

A substrate in an amount of 1.5 mM was dissolved in 50 mM BES[N,N-bis(2-hydroxyethyl)-2-aminoethanesulfonic acid]-NaOH buffer solution (pH 7.6, containing 20 mM NaCl and 2 mM CaCl$_2$). The resulting solution in an amount of 50 μl was mixed with 5 μl of human pancreas-derived α-amylase (HPA) or human salivary gland-derived α-amylase (HSA) and heated at 37° C. for 5 to 10 minutes. The enzymatic reaction was stopped by adding 100 μl of 7.5% acetic acid solution to the reaction mixture. The amount of hydrolyzed product by α-amylase in a sample was obtained by HPLC.

Results

The results are shown in Table 9.

TABLE 9

| Compound No. | Substituent after —CH$_2$— attached to 6-position of non-reducing end | Hydrolysis rate | | Km (mM) | | Pancreas type, hydrolyzed product | | | Saliva type, hydrolyzed product | | |
|---|---|---|---|---|---|---|---|---|---|---|---|
| | | Pancreas | Saliva | Pancreas | Saliva | G3P | G2P | GP | G3P | G2P | GP |
| 1 | —S—CH$_2$—C$_6$H$_5$ | 1.1 | 1.0 | 0.13 | 0.12 | 0 | 76 | 24 | 0 | 92 | 8 |
| 2 | —S—CH$_2$—C$_6$H$_4$—CH$_3$ | 1.0 | 0.9 | 0.17 | 0.17 | 0 | 78 | 22 | 0 | 93 | 7 |
| 3 | —S—CH$_2$—C$_6$H$_4$—C(CH$_3$)$_3$ | 1.0 | 0.5 | 0.65 | 0.33 | 0 | 84 | 16 | 0 | 95 | 5 |

TABLE 9-continued

| | | | | | | | | | | | |
|---|---|---|---|---|---|---|---|---|---|---|---|
| 4 | $-S-CH_2-CH_2-C_6H_5$ | 1.7 | 1.2 | 0.17 | 0.11 | 0 | 74 | 26 | 0 | 90 | 10 |
| 5 I | (S form) $-S-C^*H(CH_3)(C_6H_5)$ | 1.2 | 0.7 | 0.37 | 0.25 | 0 | 59 | 41 | 0 | 80 | 20 |
| 5 II | (R form) $-S-C^*H(CH_3)(C_6H_5)$ | 1.7 | 1.4 | 0.13 | 0.08 | 0 | 88 | 12 | 0 | 96 | 4 |
| 6 | $-S-(CH_2)_n-CH_3$ n = 1 | 2.7 | 2.1 | 0.48 | 0.33 | 0 | 68 | 32 | 0 | 87 | 13 |
| 7 | $-S-(CH_2)_n-CH_3$ n = 2 | 2.1 | 1.3 | 0.30 | 0.18 | 0 | 74 | 26 | 0 | 89 | 11 |
| 8 | $-S-(CH_2)_n-CH_3$ n = 3 | 2.7 | 2.0 | 0.29 | 0.21 | 0 | 71 | 29 | 0 | 88 | 12 |
| 9 | $-S-(CH_2)_n-CH_3$ n = 4 | 2.5 | 1.9 | 0.22 | 0.19 | 0 | 59 | 41 | 0 | 83 | 17 |
| 10 | $-S-(CH_2)_n-CH_3$ n = 5 | 2.3 | 1.7 | 0.27 | 0.20 | 0 | 62 | 38 | 0 | 85 | 15 |
| 11 | $-S-(CH_2)_n-CH_3$ n = 6 | 2.1 | 1.6 | 0.50 | 0.46 | 0 | 67 | 33 | 0 | 88 | 12 |
| 14 | $-S-CH(CH_3)_2$ | 1.9 | 1.7 | 0.27 | 0.25 | 0 | 79 | 21 | 0 | 93 | 7 |
| 15 | $-S-CH_2-CH(CH_3)_2$ | 1.8 | 1.5 | 0.20 | 0.16 | 0 | 81 | 19 | 0 | 93 | 7 |
| 16 | $-S-CH(CH_3)-CH_2-CH_3$ (racemic modification) | 1.9 | 1.6 | 0.25 | 0.21 | 0 | 76 | 24 | 0 | 91 | 9 |
| 17 | $-S-CH_2-CH_2-CH(CH_3)_2$ | 2.2 | 1.9 | 0.17 | 0.16 | 0 | 67 | 33 | 0 | 86 | 14 |
| 18 | $-S-CH_2-CH_2-N(CH_2-CH_3)_2$ | 1.1 | 0.5 | 0.50 | 0.46 | 0 | 27 | 73 | 0 | 53 | 47 |
| 19 | $-S-CH_2-CH_2-N(CH_3)_2$ | 1.0 | 0.4 | 0.45 | 0.32 | 0 | 29 | 71 | 0 | 56 | 44 |
| 20 | $-S-CH_2-CH_2-CH_2-N(CH_3)_2$ | 0.8 | 0.6 | 0.30 | 0.34 | 0 | 47 | 53 | 0 | 72 | 28 |
| 21 | $-S-CH_2-CH_2-N(piperidyl)$ | 0.7 | 0.4 | 0.26 | 0.22 | 0 | 30 | 70 | 0 | 55 | 45 |
| 22 | $-S-CH_2-CH_2-CH_2-N(piperidyl)$ | 0.6 | 0.3 | 0.18 | 0.13 | 0 | 52 | 48 | 0 | 72 | 28 |

TABLE 9-continued

| # | Structure | | | | | | | | | | |
|---|---|---|---|---|---|---|---|---|---|---|---|
| 23 | —S—CH₂—CH₂—N(morpholine, O) | 2.6 | 1.4 | 0.62 | 0.39 | 0 | 45 | 55 | 0 | 73 | 27 |
| 24 | —S—CH₂—CH₂—CH₂—N(piperazine, NH) | 0.9 | 0.7 | 0.15 | 0.12 | 0 | 72 | 28 | 0 | 87 | 13 |
| 25 | —S—CH₂-(2-pyridyl) | 1.8 | 1.7 | 0.33 | 0.26 | 0 | 73 | 27 | 0 | 89 | 11 |
| 26 | —S—CH₂-(3-pyridyl) | 2.0 | 1.7 | 0.20 | 0.15 | 0 | 74 | 26 | 0 | 90 | 10 |
| 27 | —S—CH₂-(4-pyridyl) | 1.6 | 1.5 | 0.16 | 0.15 | 0 | 83 | 17 | 0 | 93 | 7 |
| 28 | —S—CH₂-(2-nitrophenyl) | 1.7 | 1.2 | 0.27 | 0.20 | 0 | 76 | 24 | 0 | 90 | 10 |
| 29 | —S—CH₂—CH₂—N(piperidine) | 0.8 | 0.5 | 0.38 | 0.41 | 0 | 26 | 74 | 0 | 49 | 51 |
| 30 | —S—CH₂—CH₂—CH₂—C₆H₅ | 1.8 | 1.3 | 0.21 | 0.13 | 0 | 50 | 50 | 0 | 77 | 23 |
| 31 | —S—CH₃ | 2.0 | 1.6 | 0.30 | 0.25 | 0 | 54 | 46 | 0 | 78 | 22 |
| 36 I | —S(=O)—CH₂—C₆H₄—CH₃ (R form) | 1.2 | 0.5 | 0.69 | 0.45 | 0 | 47 | 53 | 0 | 70 | 30 |
| 36 II | (S form) | 0.7 | 0.2 | 0.48 | 0.23 | 0 | 27 | 73 | 0 | 50 | 50 |
| 37 | —S(=O)—(CH₂)₅—CH₃  I | 1.5 | 0.8 | 0.55 | 0.35 | 0 | 53 | 47 | 0 | 74 | 26 |
|  | II | 0.9 | 0.6 | 0.48 | 0.48 | 0 | 15 | 85 | 0 | 30 | 70 |
| 39 | —SO₂—CH₂—C₆H₄—CH₃ | 2.1 | 0.7 | 0.40 | 0.22 | 0 | 12 | 88 | 0 | 29 | 71 |
| 40 | —SO₂—(CH₂)₅—CH₃ | 2.4 | 1.2 | 0.45 | 0.27 | 0 | 10 | 90 | 0 | 21 | 79 |
| Comparative Example | BG5P  —O—CH₂—C₆H₅ | 1.4 | 1.4 | 0.11 | 0.10 | 0 | 95 | 5 | 0 | 98 | 2 |

TABLE 9-continued

| | | | | | | | | | | | |
|---|---|---|---|---|---|---|---|---|---|---|---|
| FG5P | —NH—N⟨⟩ | | 1.2 | 1.5 | 0.26 | 0.41 | 0 | 70 | 30 | 0 | 83 | 17 |

Note
(1) *means asymmetric center.
(2) (S) and (R) show steric configurations.

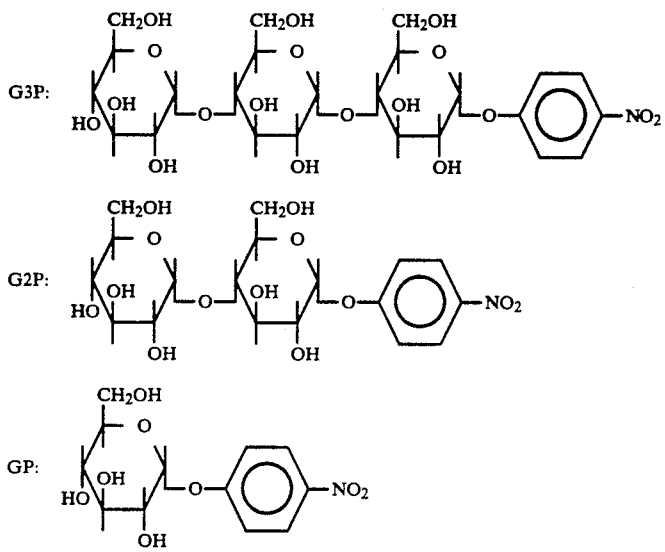

As is clear from Table 9, the oligosaccharide derivatives of the formula [I] have the following advantages as substrates for measuring α-amylase activity:

(1) The hydrolysis rate is fast (Compound Nos. 4, 5-II, 6-11, 14-17, 23, 25-27, 31 and 39 are faster than the substrate BG5P disclosed in Japanese Patent Unexamined Publication No. 1-45391 in the hydrolysis rate, and particularly Compound Nos. 6, 8 and 23 are about 2 times as sensitive as BG5P).

(2) Discrimination is better than the substrate FG5P in the fractional measuring described in Japanese Patent Unexamined Publication No. 63-39600 (EP 0260414) (Compound Nos. 23 and 29 have about 1.35 times and 1.25 times as large in discrimination as FG5P, respectively).

(3) Since the hydrolysis rate for pancreas type α-amylase is faster than that for saliva type α-amylase in every case, these oligosaccharide derivatives can sufficiently be used as a substrate for measuring pancreas type α-amylase activity (among them, Compound No. 39 has the hydrolysis rate for pancreas type α-amylase 3 times as large as that for saliva type α-amylase, and about 1.5 times as large as that of BG5P for pancreas type α-amylase). Therefore, the using amount of inhibiting substance for saliva type α-amylase can be reduced. Further, since the sensitivity for pancreas type α-amylase is high, so that the use of these substrates are particularly effective.

EXAMPLE 47

Measurement of hydrolyzed product ratios and hydrolysis rates by α-amylase in the presence of $NaN_3$ using various oligosaccharide derivatives as substrate

Procedure

Various oligosaccharide derivatives shown in Table 10 were used as substrates. A substrate was dissolved in 50 mM BES [N,N-bis(2-hydroxyethyl)-2-aminoethanesulfonic acid]-NaOH buffer solution (pH 7.6, containing 20 mM NaCl and 2 mM $CaCl_2$) so as to produce a substrate solution having the concentration of substrate of 1.4 mM. To this substrate solution, 1M $NaN_3$ was added as an activating agent. On the other hand, a substrate solution containing no activating agent was also used for the measurement.

To 1 ml of a substrate solution 100 μl of human pancreas type α-amylase (HPA) or human saliva type α-amylase (HSA) was added and reacted at 37° C. for 15 minutes. The reaction was stopped by adding 100 μl of 7.5% acetic acid to the reaction solution. The resulting products were confirmed by HPLC. The hydrolyzed product ratios and hydrolysis rates were obtained by a conventional method.

Results

Measured results are shown in Tables 10 and 11.

As is clear from Tables 10 and 11, all of 2-chloro-4-nitrophenylmaltotrioside (G3C) and derivatives thereof (Compound Nos. 32 and 42) and 2-chloro-4-nitrophenylmaltotetraoside (G4C) and derivatives thereof (Compound Nos. 33 and 43) produce 2-chloro-4-nitrophenol (CNP) by the addition of $NaN_3$. The production rate of CNP also increases as fast as 4 to 56 times by the addition of $NaN_3$.

In the case of G4C, the total α-amylase activities lower in the presence of $NaN_3$, while the total α-amylase activities increase in the cases of Compound Nos. 33 and 43 wherein the non-reducing end is blocked. This seems to be the effect obtained by introducing the modifying groups into the 6-position of non-reducing end glucose units. Further, in G4C and Compound Nos. 33 and 43, CNP is produced significantly by the addition of $NaN_3$.

From the results mentioned above, it becomes possible to measure α-amylase activity without using a coupling enzyme in the presence of an activating agent, when Compound Nos. 32, 33, 42 and 43 are used.

TABLE 10

| Substrate | Addition of NaN₃ | Pancreas type hydrolyzed product % | | | Saliva type hydrolyzed product % | | |
|---|---|---|---|---|---|---|---|
| | | G2C | GC | CNP | G2C | GC | CNP |
| G3C | No | 17 | 9 | 73 | 15 | 21 | 64 |
| | Yes | 10 | 1 | 90 | 6 | 1 | 94 |
| Compound No. 32 | No | 0 | 0 | 100 | 0 | 0 | 100 |
| | Yes | 0 | 0 | 100 | 0 | 0 | 100 |
| Compound No. 42 | No | 0 | 0 | 100 | 0 | 0 | 100 |
| | Yes | 0 | 0 | 100 | 0 | 0 | 100 |
| G4C | No | 70 | 26 | 4 | 87 | 12 | 2 |
| | Yes | 26 | 15 | 59 | 41 | 8 | 50 |
| Compound No. 33 | No | 0 | 60 | 40 | 0 | 49 | 51 |
| | Yes | 0 | 8 | 92 | 0 | 7 | 93 |
| Compound No. 43 | No | 0 | 32 | 68 | 0 | 40 | 60 |
| | Yes | 0 | 2 | 98 | 0 | 1 | 99 |

TABLE 11

| Substrate | Addition of NaN₃ | HPA G2C + GC + CNP (Total) | | CNP | | HSA G2C + GC + CNP (Total) | | CNP | |
|---|---|---|---|---|---|---|---|---|---|
| G3C | No | 0.039 ↓ | 5.1 times | 0.029 ↓ | 6.2 times | 0.015 ↓ | 7.1 times | 0.010 ↓ | 10.4 times |
| | Yes | 0.200 | | 0.180 | | 0.109 | | 0.102 | |
| Compound No. 32 | No | — | | 0.007 ↓ 0.071 | 10.5 | — | | 0.010 ↓ 0.059 | 6.1 |
| Compound No. 42 | No | — | | 0.002 ↓ 0.057 | 25.7 | — | | 0.001 ↓ 0.043 | 56.2 |
| G4C | No | 0.289 ↓ | 0.6 | 0.012 ↓ | 8.1 | 0.222 ↓ | 0.5 | 0.003 ↓ | 16.9 |
| | Yes | 0.166 | | 0.099 | | 0.114 | | 0.058 | |
| Compound No. 33 | No | 0.045 ↓ | 2.8 | 0.018 ↓ | 6.4 | 0.030 ↓ | 2.3 | 0.015 ↓ | 4.1 |
| | Yes | 0.123 | | 0.113 | | 0.068 | | 0.063 | |
| Compound No. 43 | No | 0.030 ↓ | 5.2 | 0.021 ↓ | 7.6 | 0.008 ↓ | 7.1 | 0.005 ↓ | 11.6 |
| | Yes | 0.160 | | 0.156 | | 0.055 | | 0.054 | |
| BG5P | No | 1 | | 1 | | 1 | | 1 | |

Note) Values in Table 11 are relative values taking the hydrolysis rate using BG5P as a substrate as 1 mM/min.

In Tables 10 and 11, G2C, GC and CNP means as follows:

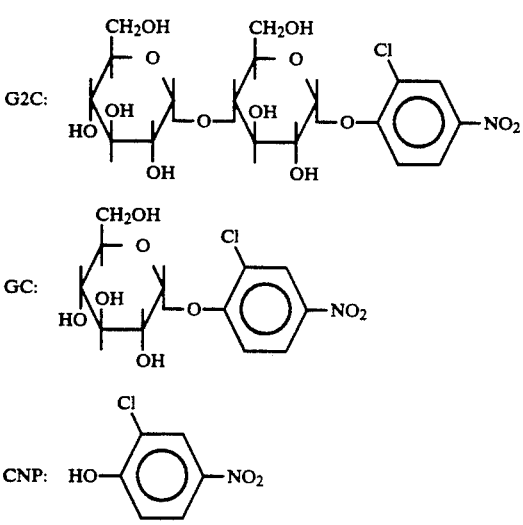

EXAMPLE 48

Measurement of α-amylase activity

Procedure

A measuring reagent solution was prepared by dissolving 90 mg of Compound No. 8 or 90 mg of p-nitrophenyl O-{6-O-(benzyl-α-D-glucopyranosyl)-(1→4)}-tris{O-α-D-glucopyranosyl-(1→4)}-α-D-glucopyranoside (BG5P) in 30 ml of 50 mmol/l. BES-NaOH buffer solution (pH 7.6) containing 400 units of glucoamylase, 300 units of α-glucosidase, 20 mmol/l of NaCl and 2 mmol/l of CaCl₂.

Measuring method

To 2 ml of a sample, 100 μl of serum sample was added and heated at 37° C. Absorbance change of this reaction solution at a wavelength of 405 nm was measured.

On the other hand, a calibration curve was obtained in the same manner as mentioned above except for using a standard sample containing known α-amylase activity. From this calibration curve, α-amylase activity in the sample was obtained.

FIG. 1 is a graph showing a relationship between α-amylase activity at each diluted stage of standard samples (Somogyi unit/dl) and absorbance increasing amount per minute (ΔA) at a wavelength of 405 nm. In FIG. 1, the curve -o- shows the results obtained by using Compound No. 8 and the curve -x- shows the results obtained by using BG5P.

As is clear from FIG. 1, both calibration curves obtained by lining plotted absorbance increasing amounts (ΔA/min) against α-amylase activity (Somogyi unit/dl) become straight lines passing through O point. Both calibration curves show good quantitativeness, but Compound No. 8 is about 1.7 times as sensitive as BG5P.

EXAMPLE 49

Discrimination measurement of α-amylase activities (Measuring reagent solutions)

(1) First solution

A first solution was prepared by dissolving 300 mg of Compound No. 23 or 300 mg of p-nitrophenyl O-[6- deoxy-6-{(2-pyridyl)amino}-α-D-glucopyranosyl]-(1→4)-tris{O-α-D-glucopyranosyl-(1→4)}-α-D-glucopyranoside (FG5P), and 25 units of isomaltase in 500 ml of 0.08M 3.3-dimethylglutaric acid-NaOH buffer solution (pH 6.9, containing 20 mmol/l of NaCl).

(2) Second solution

A second solution was prepared by dissolving 300 mg of Compound No. 23 or FG5P, and 1150 units of α-glucosidase in 50 ml of 0.08M 3,3-dimethylglutaric acid-NaOH buffer solution (pH 6.9, containing 20 mmol/l of NaCl).

(3) Enzymatic sample solution

Human saliva type α-amylase (mfd. by Sigma Chemical Co.) and human pancreas type α-amylase prepared from human pancreatic juice were each adjusted to 5.5 units/l. and mixed so as to make the ratio (v/v) 3:1, 1:1 and 1:3, respectively.

Measuring method

To 300 μl of a first solution or second solution previously heated at 30° C., 50 μl of an enzymatic sample solution was added and mixed well, while maintaining the temperature at 30° C. Absorbance of this reaction solution with the lapse of time at 400 nm was measured. As a blank test, when a first solution was used, a mixture obtained by adding 50 μl of pure water to the first solution was used, and when a second solution was used, a mixture obtained by adding 50 μl of pure water to the second solution was used. Then, a changing rate of absorbance in the first solution ($\Delta E_1$/min) and that in the second solution ($\Delta E_2$/min) were obtained and used for calculating the ratio of $$\frac{\Delta E_1/\text{min}}{\Delta E_2/\text{min}}.$$

FIG. 2 is a graph showing a relationship between $\Delta E_1$/min/$\Delta E_2$/min and human pancreas type α-amylase activity ratio. In FIG. 2, the curve -o- shows the results obtained by using Compound No. 23 and the curve -x- shows the results obtained by using FG5P.

As is clear from FIG. 2, there can be obtained good linealities in both cases between the $\Delta E_1$/min/$\Delta E_2$/min and the human pancreas type α-amylase activity ratio. But Compound No. 23 has better characteristics to discriminate α-amylase isozymes as high as about 1.35 times compared with FG5P.

As mentioned above, the oligosaccharide derivatives of the formula [I] are remarkably useful as substrates for measuring α-amylase activity and for measuring each isozyme activity of human α-amylase, and also as substrates for specifically measuring pancreas type α-amylase activity. These oligosaccharide derivatives [I] have advantages compared with the same known substrates in that the sensitivity is higher, the discrimination is more excellent, and when used as a substrate for specifically measuring pancreas type α-amylase, the adding amount of a saliva type α-amylase inhibiting substance can be reduced remarkably and the sensitivity is good. Further, the oligosaccharide derivatives of the formula [I] can be easily synthesized compared with known oligosaccharide derivatives of the same kind (known oligosaccharide derivatives having various substituents via an oxygen atom at the 6-position of reducing end glucose unit).

What is claimed is:

1. An oligosaccharide derivative of the formula:

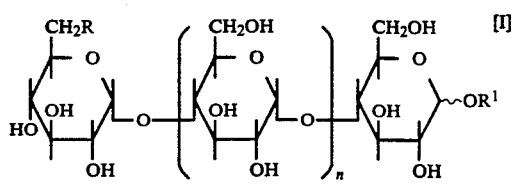

wherein R is —SR²,

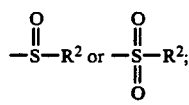

R² is an alkyl group or a substituted alkyl group; R¹ is an optically detectable group or a hydrogen atom; and n is zero or an integer of 1 to 5.

2. An oligosaccharide derivative according to claim 1, which is represented by the formula:

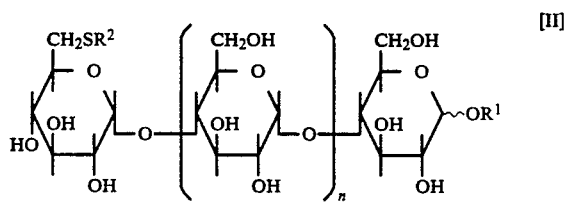

wherein R² is an alkyl group or a substituted alkyl group; R¹ is an optically detectable group or a hydrogen atom; and n is zero or an integer of 1 to 5.

3. An oligosaccharide derivative according to claim 1, which is represented by the formula:

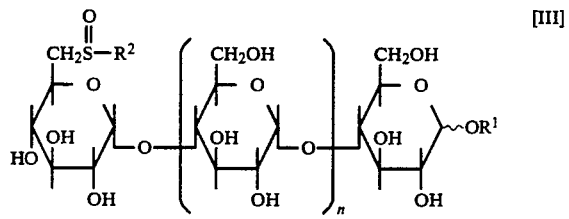

wherein R² is an alkyl group or a substituted alkyl group; R¹ is an optically detectable group or a hydrogen atom; and n is zero or an integer of 1 to 5.

4. An oligosaccharide derivative according to claim 1, which is represented by the formula:

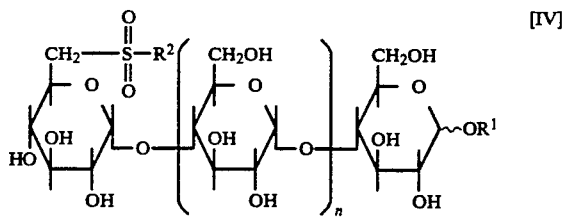

wherein R² is an alkyl group or a substituted alkyl group; R¹ is an optically detectable group or a hydrogen atom; and n is zero or an integer of 1 to 5.

5. An oligosaccharide derivative according to claim 2, which is represented by the formula:

6. An oligosaccharide derivative according to claim 2, which is represented by the formula:
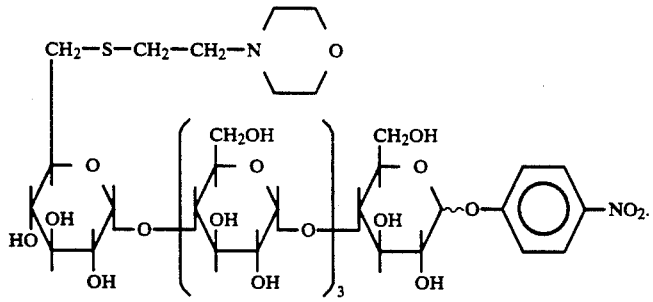
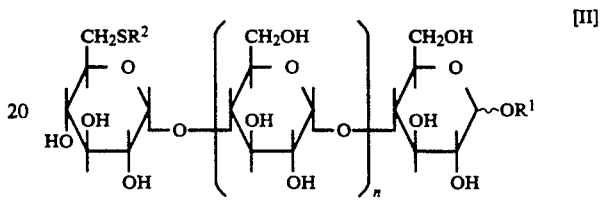
wherein $R^2$ is a substituted alkyl group; $R^1$ is an optically detectable group; and n is an integer of 1 to 5.
* * * * *